(12) United States Patent
Abukhalaf

(10) Patent No.: US 12,131,671 B1
(45) Date of Patent: Oct. 29, 2024

(54) BEVERAGE CONTAINERS

(71) Applicant: Zaid A. Abukhalaf, San Jose, CA (US)

(72) Inventor: Zaid A. Abukhalaf, San Jose, CA (US)

(*) Notice: Subject to any disclaimer, the term of this patent is extended or adjusted under 35 U.S.C. 154(b) by 346 days.

(21) Appl. No.: 17/591,607

(22) Filed: Feb. 3, 2022

Related U.S. Application Data

(60) Provisional application No. 63/145,470, filed on Feb. 3, 2021.

(51) Int. Cl.
| | |
|---|---|
| *B65D 85/30* | (2006.01) |
| *B65D 23/16* | (2006.01) |
| *B65D 85/72* | (2006.01) |
| *G01K 13/00* | (2021.01) |
| *G01N 33/14* | (2006.01) |
| *G08B 21/18* | (2006.01) |
| *G09F 9/30* | (2006.01) |
| *H02J 50/10* | (2016.01) |
| *H04Q 9/00* | (2006.01) |
| G01S 19/14 | (2010.01) |
| G09F 3/02 | (2006.01) |

(52) U.S. Cl.
CPC ............ *G09F 9/301* (2013.01); *B65D 23/16* (2013.01); *B65D 85/72* (2013.01); *G01K 13/00* (2013.01); *G01N 33/146* (2013.01); *G08B 21/182* (2013.01); *H02J 50/10* (2016.02); *H04Q 9/00* (2013.01); *B65D 2203/00* (2013.01); *G01S 19/14* (2013.01); *G09F 2003/0273* (2013.01); *H04Q 2209/40* (2013.01)

(58) Field of Classification Search
CPC .. G01N 33/146; B65D 85/30; B65D 85/8043; B65B 85/72
See application file for complete search history.

(56) References Cited

U.S. PATENT DOCUMENTS

| | | | |
|---|---|---|---|
| 4,747,497 A * | 5/1988 | Holman ................. | B65D 55/02 215/230 |
| 4,883,187 A | 11/1989 | Knitzer | |
| 6,840,100 B1 | 1/2005 | Wotiz | |
| 7,663,497 B2 | 2/2010 | Chishima et al. | |

(Continued)

FOREIGN PATENT DOCUMENTS

KR          101182382          2/2012

*Primary Examiner* — Steven Lim
*Assistant Examiner* — Son M Tang
(74) *Attorney, Agent, or Firm* — Makoui Law, PC; Ali Makoui

(57) ABSTRACT

A beverage container includes a processor, an electronic display, and one or more sensors. The beverage container includes a beverage compartment for human consumption and a sample compartment for storing a sample of the same beverage stored in the beverage compartment for measuring parameters of the beverage over time. The sensors read parameters related to the beverage and the container. The processor determines the quality of wine in a wine bottle, the temperature history of the wine bottle, and the percentage of time the wine bottle has been stored horizontally. The processor determines whether the beverage in a carbonated beverage container may spill after the container is shaken. The processor determines whether opening of a champagne bottle may result in the cork to pop up. The processor may display customized messages and animations on the electronic display. The processor changes the language used to display based on the container's location.

9 Claims, 30 Drawing Sheets

(56) References Cited

U.S. PATENT DOCUMENTS

| | | |
|---|---|---|
| 8,373,574 B2 | 2/2013 | Gebhard |
| 8,550,288 B2 | 10/2013 | Briar et al. |
| 8,717,182 B1 * | 5/2014 | Brashears .......... G06K 7/10722 |
| | | 340/572.1 |
| 9,382,107 B2 | 7/2016 | Pfeiffer et al. |
| 9,930,980 B2 * | 4/2018 | Pau ....................... A47G 23/16 |
| 10,368,666 B2 | 8/2019 | Yekutiely |
| 10,464,331 B2 | 11/2019 | Naito et al. |
| 10,676,251 B2 * | 6/2020 | Krafft .................... B65D 51/24 |
| 10,717,569 B1 | 7/2020 | Bowles |
| 2005/0242120 A1 * | 11/2005 | Sato ...................... G07F 13/065 |
| | | 222/146.6 |
| 2010/0196556 A1 * | 8/2010 | Wheeler ................ B65D 85/78 |
| | | 222/386 |
| 2014/0311239 A1 | 10/2014 | Marjanovic et al. |
| 2016/0001936 A1 * | 1/2016 | Rap .................... B65D 47/2031 |
| | | 156/263 |
| 2017/0042373 A1 * | 2/2017 | Alexander .......... A47J 31/4417 |
| 2019/0236429 A1 * | 8/2019 | Shinohara .............. B65D 41/62 |
| 2019/0318610 A1 * | 10/2019 | Tsang ...................... H04W 4/35 |
| 2020/0157479 A1 * | 5/2020 | Nunes Nogueira .... C12M 41/30 |
| 2024/0142169 A1 * | 5/2024 | Kosa ..................... F25D 31/006 |

* cited by examiner

BEVERAGE CONTAINERS

CLAIM OF BENEFIT TO PRIOR APPLICATIONS

This application claims the benefit of U.S. Provisional Patent Application Ser. No. 63/145,470, filed on Feb. 3, 2021. The contents of U.S. Provisional Patent Application 63/145,470 are hereby incorporated by reference.

BACKGROUND

Beverage containers, including cans and bottles of beverage, are used to store a variety of beverages such as wines, beers, and soft drinks. The information about the contents of a beverage container is typically limited to what is printed or painted on the outside of the beverage container.

In addition, the present condition of the beverage inside the container is not easily discernable by just looking at the beverage container. For example, it may not be possible to determine whether a bottle of wine has turned into vinegar without opening the bottle. It may not be possible to determine the past history of the wine bottle, for example, whether the bottle has gone through extreme temperature changes. If a bottle or can of carbonated soda is shaken, it may not be possible to determine whether or not the beverage may spill out if the bottle or the can is opened.

BRIEF DESCRIPTION OF THE DRAWINGS

The various embodiments of the present beverage containers now will be discussed in detail with an emphasis on highlighting the advantageous features. These embodiments depict the novel and non-obvious beverage containers shown in the accompanying drawings, which are for illustrative purposes only. These drawings include the following figures, in which like numerals indicate like parts.

DETAILED DESCRIPTION

Figure 1A:
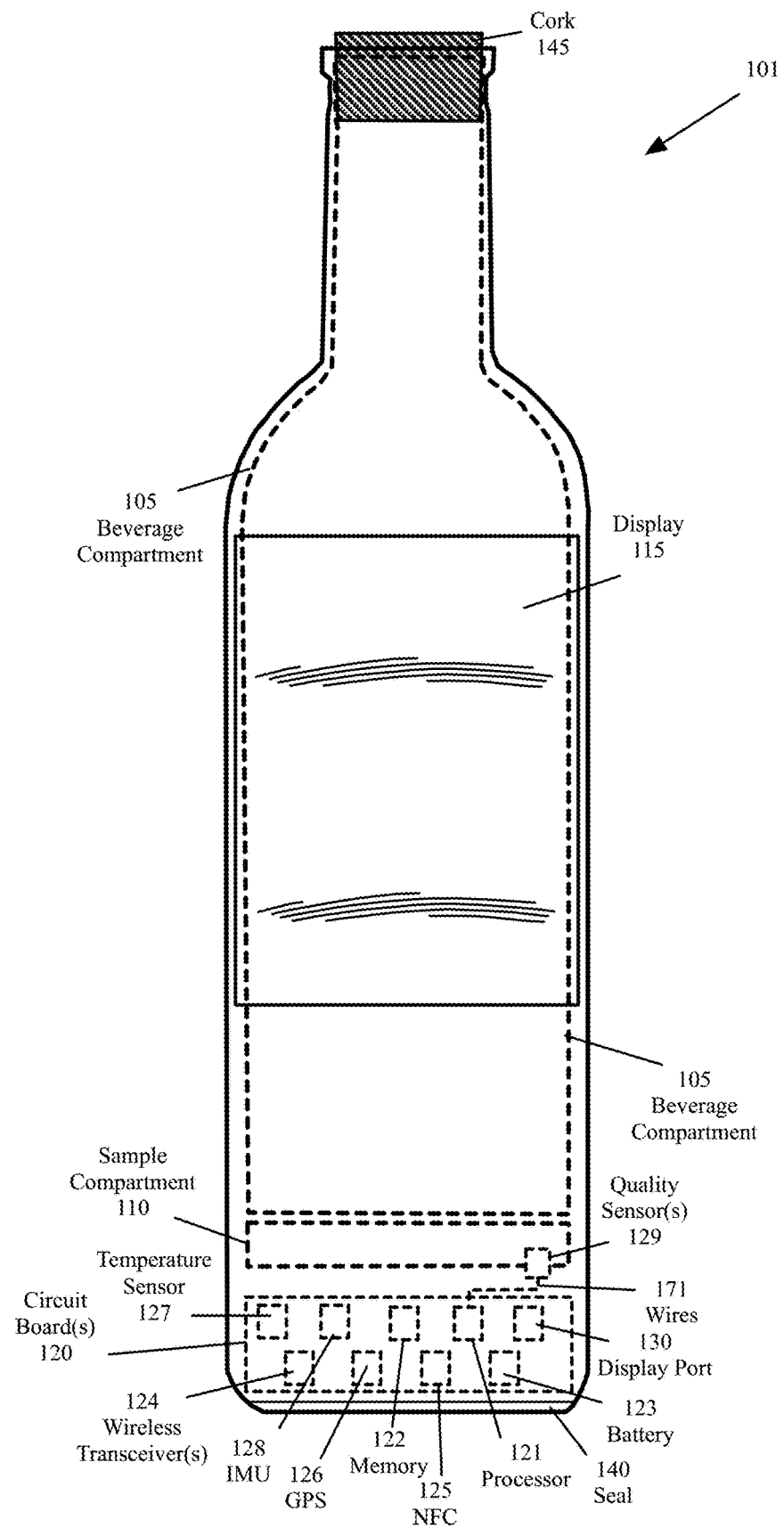
FIG. 1A is a functional diagram illustrating an example wine bottle, according to various aspects of the present disclosure.

One aspect of the present embodiments includes the realization that the information provided by the existing beverage containers about the beverage in the container is limited to the static information printed or painted on the beverage container. The information is provided in one or more languages and there is not an easy way of changing the information to another language should the beverage container is shipped or carried to a region that speaks a different language.

In addition, the existing sealed beverage containers do not provide any indication of the current condition of the beverage inside the container. For example, it may not be possible to determine whether a bottle of wine has turned into vinegar without opening the bottle. It may not be possible to determine the past history of the wine bottle, for example, whether the wine bottle has been stored horizontally and/or whether the wine bottle has been stored in an environment with a controlled temperature. Furthermore, it may not be possible to determine whether or not a carbonated beverage in a sealed container may spill out if the container is opened.

The present embodiments, as described in detail below, solve the above-mentioned problems by providing beverage containers that may include a processor, an electronic display, and one or more sensors. The beverage containers may include a beverage compartment for human consumption. The beverage containers may include a sample compartment for storing a sample of the same beverage that is stored in the beverage compartment for measuring one or more parameters of the beverage over time.

Depending on the type of the beverage container and the type of the beverage, the sensors may read different parameters related to the beverage and/or related to the beverage container and may provide the parameters to the processor. The sensors may include a temperature sensor, an accelerometer, a magnetometer, a gyroscope, one or more quality sensors, a pressure sensor, a force sensing resistor, etc. The processor may determine the quality of wine in a wine bottle. The processor may determine the temperature history of the wine bottle. The processor may determine the percentage of time the wine bottle has been stored horizontally.

The processor may determine whether the beverage in a carbonated beverage container may spill after the beverage container has been shaken. The processor may determine whether any excess gas that has been released in the beverage compartment is dissolved back into the liquid beverage. The processor may determine whether or not opening of a champagne bottle may result in the cork to pop up.

The processor may include one or more wireless transceivers and/or an NFC chip and may wirelessly communicate with one or more authorized external electronic devices through the wireless transceiver(s) and/or through the NFC chip. The beverage container may include one or more chargeable batteries that may be charged through the wireless transceiver(s) and/or through the NFC chip.

The beverage container may store messages and/or animations to display on the electronic display of the beverage container. The processor of the beverage container may also receive customized messages and/or animations from authorized external electronic devices to display on the electronic display of the beverage container. The messages may include information regarding the beverage container, information regarding the contents of the beverage container, advertisements, messages regarding an event, instructions for updating software, instructions for performing diagnostics, instructions for changing language, instructions for generating customized messages, etc.

The beverage container may include non-volatile memory to store instructions for the processor to execute. The beverage container may include read-write memory to store sensor data, messages, and/or animations. The beverage container may include one or more small speakers, such as piezo-electric speakers, to play sounds and music. The processor may include a global positioning system (GPS) receiver and/or may receive GPS data and/or location information from the external electronic devices. The processor, in response to receiving the GPS data and/or location information, and/or upon receiving one or more signals, may change the language used to display and/or to play messages.

The remaining detailed description describes the present embodiments with reference to the drawings. In the drawings, reference numbers label elements of the present embodiments. These reference numbers are reproduced below in connection with the discussion of the corresponding drawing features.

I. Beverage Containers with Electronic Display

Some of the present embodiments provide a beverage container such as, a beverage can or a beverage bottle that may include at least one processor and an electronic display. The beverage container may, for example, and without limitations, be a wine bottle, a champagne bottle, a soda can, or a soda bottle. The beverage container may include one or more sensors for measuring different parameters of the beverage and/or the beverage container's environment. The display may be a flexible display attached to the exterior of the beverage container. The processor may be located inside the beverage container and may be communicatively coupled with the display by a wired link and/or by a wireless link. The processor may display the measured parameters and/or one or more messages on the display.

The message(s) may be customizable and may translate to a different language based on different criteria. The messages may include information regarding the beverage container, information regarding the contents of the beverage container, advertisements, messages regarding an event, instructions for updating software, instructions for performing diagnostics, instructions for changing language, instructions for generating customized messages, etc.

Figure 1B:
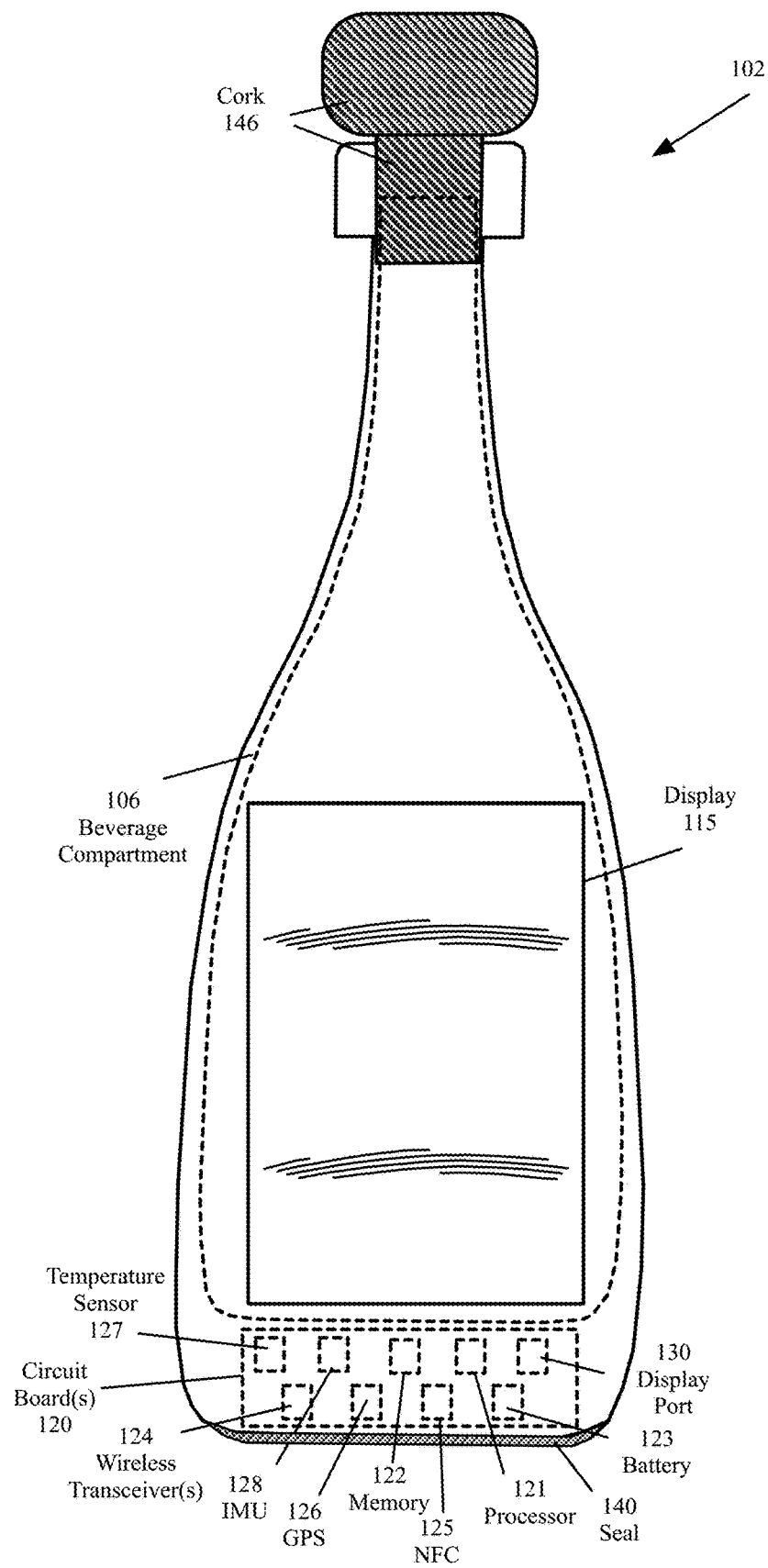
FIG. 1B is a functional diagram illustrating an example carbonated beverage bottle, according to various aspects of the present disclosure.
Figure 1C:
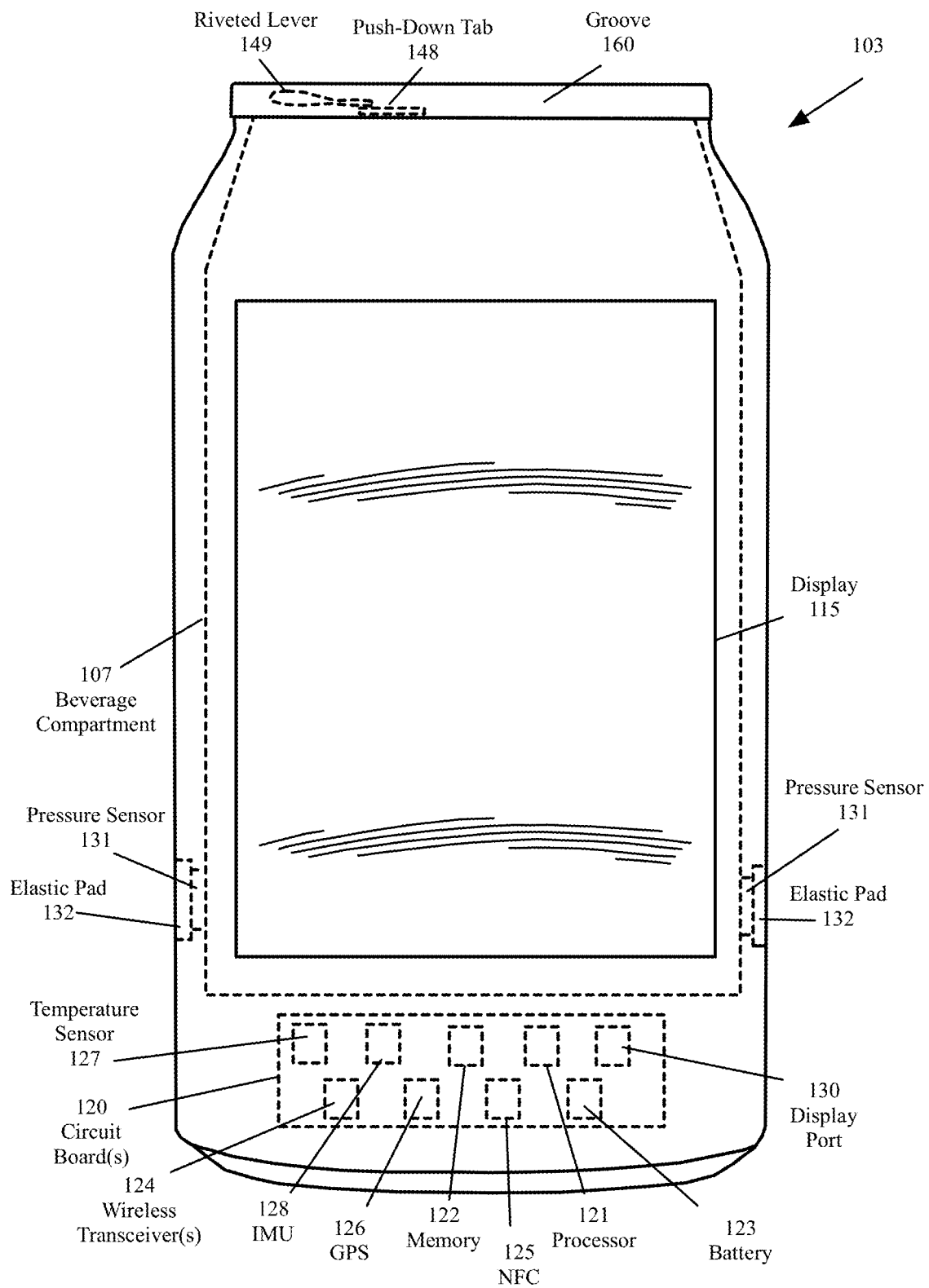
FIG. 1C is a functional diagram illustrating an example carbonated beverage can, according to various aspects of the present disclosure.

FIG. 1A is a functional diagram illustrating an example wine bottle, according to various aspects of the present disclosure. FIG. 1B is a functional diagram illustrating an example carbonated beverage bottle, according to various aspects of the present disclosure. FIG. 1C is a functional diagram illustrating an example carbonated beverage can, according to various aspects of the present disclosure.

With reference to FIG. 1A, the wine bottle 101 may include a beverage compartment 105 (or the drinking wine compartment) to store wine for human consumption. The wine bottle 101 may include a sample compartment 110 to store a sample of the same wine that is stored in the beverage compartment to measure one or more parameters of the wine over time. The beverage compartment 105, in some embodiments, may be capped by a cork 145.

The sample compartment 110 may include a hole through which at least a portion of one or more quality sensors 129 may be inserted into the sample compartment 110. The quality sensor(s) 129 may be in contact with the wine stored in the sample compartment 110 to measure different parameters of the wine over time. The quality sensor(s) may, for example, and without limitations, measure the acidity of wine, the oxidation level of wine, etc. For example, the existence of acetic acid may be used as an indication of the wine being turned into vinegar.

The quality sensor(s) 129 may be communicatively coupled to the processor 121 by a set of wires 171. The hole in the sample compartment 110 may be sealed after the sample compartment is filled with a quantity of wine and the quality sensor(s) 129 is/are inserted in the sample compartment 110. In some embodiments, the beverage container 101 may include a seal 140 that may seal the bottom of the beverage container 101 after the sample compartment is filled, and the circuit board(s) 120 (described below) and the quality sensor(s) 129 are placed in the beverage container 101. In some embodiments, the seal 140 may be made of a material such as for example, and without limitations, plastic, vinyl polymer (e.g., polyvinyl chloride (PVC)), rubber, etc., that may be glued, screwed, or otherwise secured to the bottom of the bottle 101.

With reference to FIG. 1B, the carbonated beverage bottle 102, in some embodiments, may be a champagne bottle that may include a beverage compartment 106 to store champagne or bubbling wine for human consumption. The beverage compartment 106 may be capped by a cork 146.

In other embodiments, the carbonated beverage bottle 102 may store a carbonated beverage, such as, for example, and without limitations, soda, diet soda, beer, carbonated fruit juice, etc. The beverage compartment 106 of these embodiments may be used to store the corresponding carbonated beverage. The beverage container 102, in some of these embodiments may be made of plastic and the beverage compartment 106 may be capped by a rotating plastic cap (instead of the cork 146) that may require a plastic tab to be broken in order to open the bottle. The beverage container, in some of these embodiments, may be made of glass and the beverage compartment 106 may be covered by a metallic cap that may be opened by a bottle opener. In some embodiments, the beverage container 102 may include a seal 140 that may seal the bottom of the beverage container 102 after the circuit board(s) 120 are placed in the beverage container 102. In some embodiments, the seal 140 may be made of a material such as for example, and without limitations, plastic, vinyl polymer (e.g., PVC), rubber, etc. that may be glued, screwed, or otherwise secured to the bottom of the bottle 102.

With reference to FIG. 1C, the beverage can 103 may include a beverage compartment 107 to store beverage, such as, for example, and without limitations, beer or soda, for human consumption. The beverage compartment 107 may be capped by a push-down tab 148. The push-down tab 148 may be pushed inside the beverage compartment 107 when the riveted lever 149 is pulled up. The push-down tab 148 and the riveted lever 149 may be inside a groove 160 on top of the beverage can 103.

With reference to FIGS. 1A-1C, each one of the beverage containers 101-103 may include a display 115 and one or more circuit boards 120. The display 115 may be a flexible electronic display that may be attached to the exterior of the beverage container 101-103. The display 115, in some embodiments, may a touchscreen. Examples of the flexible display include organic light-emitting diode (OLED or organic LED), organic liquid crystal diode (LCD), Gyricon, etc.

The circuit board(s) 120 may be, for example, and without limitations, printed circuit boards (PCB). The circuit board(s) 120 may include electrical components such as, for example, and without limitations, at least one processor 121, at least one memory unit 122, at least one battery 123, one or more wireless transceivers 124, an NFC chip (or tag) 125, a GPS receiver 126, a temperature sensor 127, an inertial measurement unit (IMU) 128, one or more quality sensors 129, and/or a display port 130. The beverage container, in some embodiments, may include a force sensing resistor 131 and/or an elastic pad 132.

The processor 121 may be a microcontroller, a microprocessor, etc., that may be configured to send data to, and to receive data from, the display 115, the other electronic components 122-131 of the corresponding beverage container 101-103, and/or one or more external electronic devices. The memory unit(s) 122 may store program(s) executed by the processor. The memory unit(s) 122 may store data used by the processor 121. The memory unit(s) 122 may include volatile and non-volatile storage.

The battery 123 may provide power to the electronic components of the corresponding beverage container 101-103. The battery 123, in some embodiments may be a rechargeable battery, such as, for example, and without limitations, a lithium-ion (Li-ion) battery, a lithium-ion polymer (Li-ion polymer) battery, a nickel-cadmium (NiCd) battery, etc. As described below, the rechargeable battery may be charged using different sources of power such as NFC, ultrasound, wireless, direct current (DC) power through a universal serial bus (USB) port, etc. Although the term battery is used in several examples herein, it should be understood that more than one battery may be used in each beverage container 101-103. The batteries may be connected in series to provide more voltage, the batteries may be connected in parallel to provide more current, or some of the batteries may be connected in series and the others may be connected in parallel to boost both the current and the voltage provided by an individual battery.

The wireless transceiver(s) 124, may be, for example, and without limitations, Bluetooth, Wi-Fi, and/or infrared (IR) transceivers. The processor 121 may use the wireless transceiver(s) 124 to communicate with one or more external electronic devices (not shown) to send and receive data, to load or update software program(s) and/or firmware into the memory unit(s) 122 for execution by the processor 121, to reset the processor 121, to place the processor 121 in diagnostic mode, etc. The external electronic devices may be, for example, and without limitations, smartphones, tablets, computers, servers, etc. The external electronic devices, in some embodiments, may include an application program that may be used to interface the external electronic devices with the beverage containers 101-103.

The processor 121, in some embodiments, may use the wireless transceiver(s) 124 to communicate with the display 115. In other embodiments, the processor 121 may communicate with the display 115 through the display port 130 and a wired connection (not shown). The embodiments that the processor 121 wirelessly communicates with the display 115, may not include the display port 130.

In addition to, or in lieu of the wireless transceiver(s) 124, the beverage containers 101-103 may include an NFC chip 125. The processor 121 may use the NFC chip 125 to communicate with one or more external devices. The NFC chip 125, in some embodiments, may be used to charge the battery 123. The NFC is a short-range wireless connectivity standard that uses magnetic field induction to enable communication between devices that are brought within a close proximity (e.g., within 4 centimeters (cm) or less) of each other. An NFC chip may include non-transitory, non-volatile read-writable storage, such as, for example, and without limitation random access memory (RAM), erasable programmable read-only memories (EPROMs), electrically erasable programmable read-only memories (EEPROMs), flash memory, magnetic memory, etc. The NFC chip and an associated antenna are sometimes referred to as an NFC tag. The NFC chips may also be incorporated in mobile devices such as mobile phones, tables, laptops, etc.

When a mobile device with an NFC chip is brought to within a short distance (e.g., 4 cm or less) of the NFC chip 125 of the beverage container, the NFC chip of the mobile device may generate a magnetic field which may induce an electric current in the antenna of the NFC chip of the beverage container. The NFC chip 125 of the beverage container may act as a transponder and may modulate the data stored on the NFC chip in a magnetic field and inductively couple this magnetic field to the mobile device's NFC chip.

A GPS 126 integrated with the beverage containers 101-103 and/or a GPS of an electronic device that is wirelessly connected to the processor 121 may provide the information about the location of the corresponding beverage container 101-103. As described below, the location of the beverage container 101-103 may be used to change the language of the messages that may be displayed on the display 115.

The temperature sensor 127 may be, for example, and without limitations, a thermocouple or a thermistor. The temperature sensor 127 may be used to measure the temperature of the interior of the corresponding beverage container 101-103. The processor 121 may read the temperature parameters measured by the temperature sensor 127 and may store the parameter values in the memory 122. The processor 121 may use the temperature parameters as one of the parameters to determine the quality of the wine stored in the wine bottle 101. The processor 121 may use the temperature parameters to determine whether the beverage in a beverage container 101-103 has a predetermined temperature that, depending on the type of the beverage, may be desirable for human consumption.

The beverage containers 101-103, in some embodiments, may include an IMU 128. The IMU 128 may include one or more sensors. The IMU 128 may include an accelerometer (e.g., a three-dimensional (3D) accelerometer), a magnetometer (e.g., a 3D magnetometer), and/or a gyroscope (e.g., a 3D gyroscope). The IMU 128, in some of the present embodiments, may include one or more micro electro-mechanical system (MEMS) sensors and may be a single chip. In some embodiments, the accelerometer, the magnetometer, and/or the gyroscope may be separate sensors in different chips (e.g., and without limitations, different MEMS chips) instead of being in a single IMU chip.

As described below, the accelerometer may be used by the processor 121 to determine whether the beverage container is stationary or being moved. The magnetometer and/or the gyroscope may be used by the processor 121 to determine the orientation of the beverage container. The orientation of the beverage container may be used, for example, to adjust the orientation of the information shown on the display 115 and/or to determine whether beverage container (e.g., the wine bottle 101) has been stored in an optimal position during long term storage.

The force sensing resistor 131 may be connected wirelessly or with one or more wires (not shown) to the processor 121. As described below, in the embodiments that the beverage stored in the beverage container is carbonated and the beverage compartment 106 or 107 is flexible, the force measurements made by the force sensing resistor 131 may be used to determine whether the beverage inside the beverage compartment 107 may spill out if the beverage compartment 106 or 107 is opened.

II. Communicating with External Devices

The beverage container 101-103, in some embodiments, may communicate with one or more external electronic devices. The communication may be performed through the wireless transceiver(s) 124 and/or through the NFC 125. The beverage container, in some embodiments, may authenticate the external devices in order to communicate with them. For example, the external devices may download an application program that may be used to communicate with the beverage containers of the present embodiments.

Figure 2:
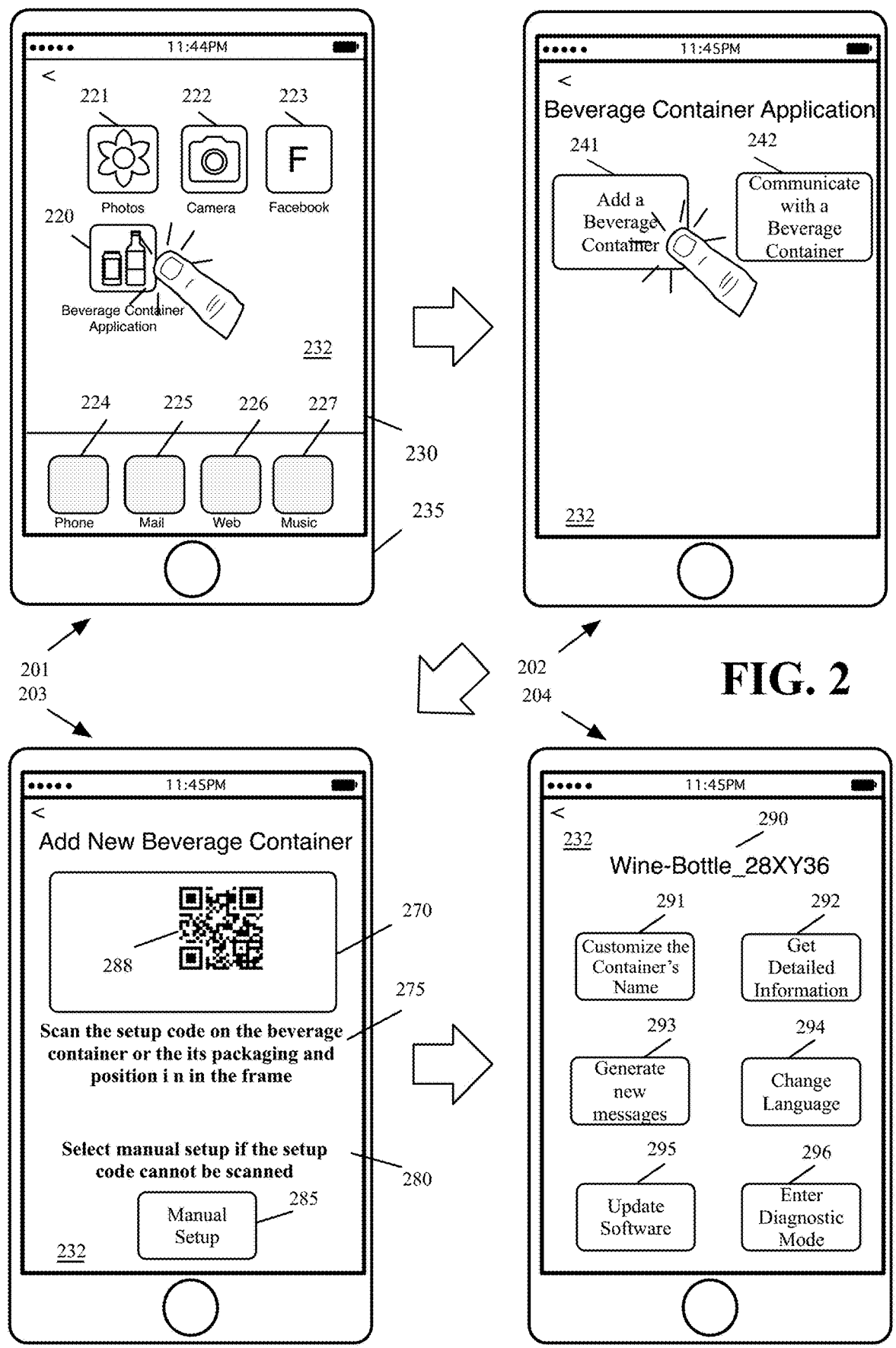
FIG. 2 illustrates a schematic front view of an electronic device that may include an application program for communicating with one or more beverage containers, according to various aspects of the present disclosure.

FIG. 2 illustrates a schematic front view of an electronic device that may include an application program for communicating with one or more beverage containers, according to various aspects of the present disclosure. The electronic device 235 may be communicatively coupled with any of the beverage containers 101-103 through a wired connection (e.g., through the USB port 1110 and cable 1130 described below with reference to FIGS. 11A-11B) or a wireless connection (e.g., through the Bluetooth transceiver, the Wi-Fi transceiver, the IR transceiver, and/or the NFC chip described above).

FIG. 2 illustrates, through four stages 201-204, an electronic device 235 using an application program 220 to communicate with one or more beverage containers. Stage 201 shows a user interface (UI) 232 displayed on a display (e.g., a touchscreen) 230 of the electronic device 235. The UI 232 may display a list of applications 220-227. The applications may include a beverage container application 220 that may be, for example, downloaded from a website or an application store.

As shown, the beverage container application 220 may be selected in stage 201. In response to the selection of the beverage container application 220, the UI 232 in stage 202 may display several options 241-242. The option 241 may be used to add new beverage containers to communicate using the application program, 220. The option 242 may be used to communicate with the beverage containers that are already added to the list of beverage containers.

As shown in stage 202, the option 241 may be selected to add a new beverage container. In response, the UI 232, in stage 203, may turn on the camera of the electronic device 235. As shown, the UI 232 in stage 203 may display a region 270 on the display 230 of the electronic device 235. The UI 232 may display a message 275 instructing the image of a setup code of the beverage container to be fitted inside the region 270. The beverage containers, in some embodiments, may include a setup code, such as, for example, and without limitations, a barcode or a quick response (QR) code. The setup code may be on the container and/or on the container's package.

The UI 232, in some embodiments, may display a message 280 and may provide an option 285 to manually enter a setup code. As shown in stage 203, the setup code 288 is fitted in the display region 270. In response, the UI 232, in stage 204, may display the name 290 of the beverage container. The name 290 of the beverage container may be the same name that is displayed on the display 115 (FIGS. 1A-1C) of the beverage containers 101-103.

The UI 232 may provide an option 291 to customize the container's name, an option 292 to get detail information about the beverage container, an option 293 to add new messages to be displayed on the beverage container, an option 294 to change the language for communicating with the beverage container and/or the language used to display messages on the display of the beverage container, an option 295 to update the software and/or the firmware of the beverage container, and/or an option 296 to enter into diagnostic mode. Further details of these options are described below.

In the embodiments that the beverage container 101-103 include an NFC chip 125, the NFC chip 125 may include the setup code. In these embodiments, the UI 232, in stage 203, may display a message (e.g., instead of the message 275) to bring the electronic device 235 to the vicinity of the beverage container 101-103 such that the setup code in the NFC chip 125 of the beverage container 101-103 may be read by the NFC chip of the electronic device 235.

Figure 3:
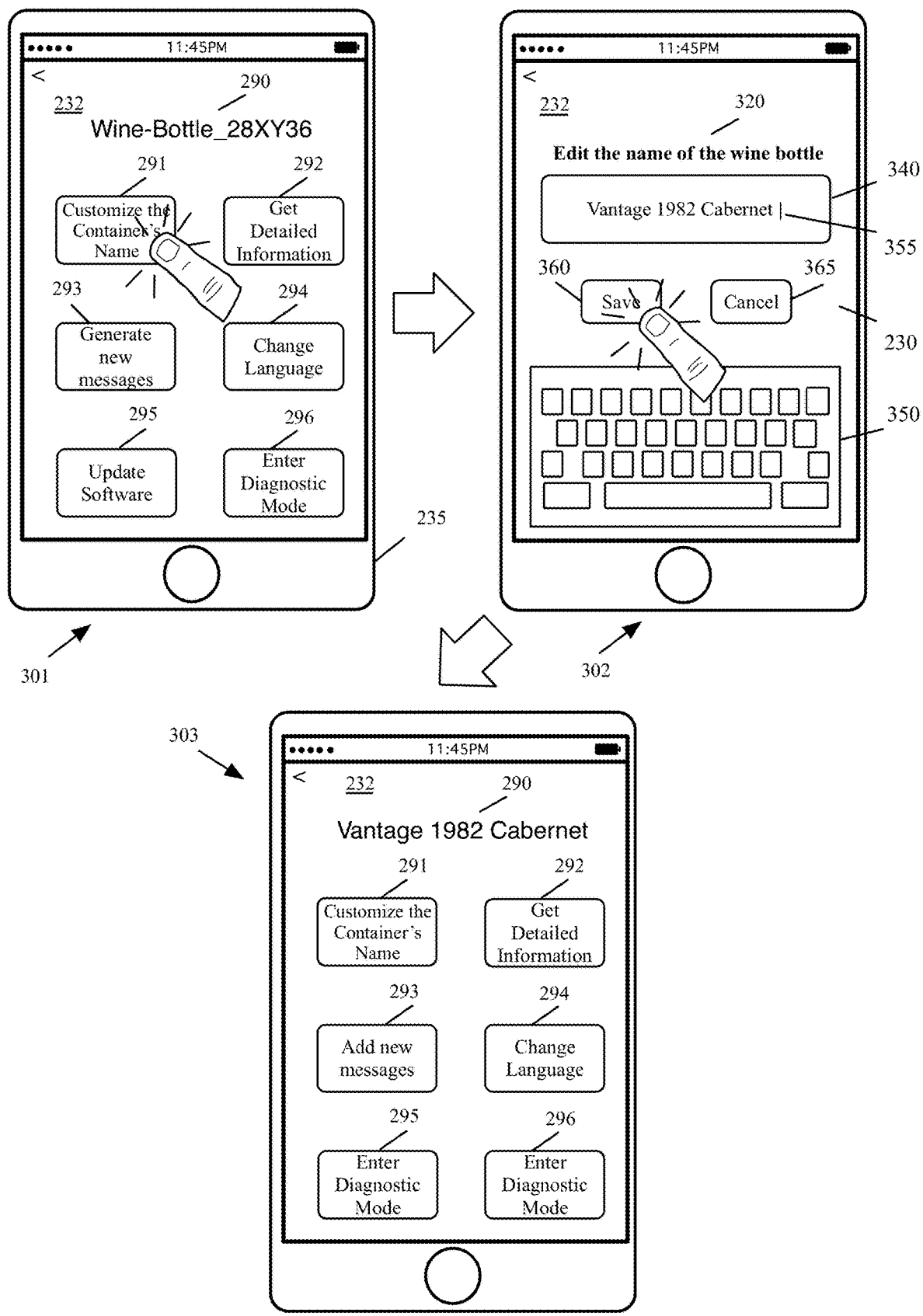
FIG. 3 illustrates a schematic front view of an electronic device that may include an application program for changing the displayed name of a beverage container, according to various aspects of the present disclosure.

FIG. 3 illustrates a schematic front view of an electronic device that may include an application program for changing the displayed name of a beverage container, according to various aspects of the present disclosure. The figure, as shown, includes three stages 301-303. Stage 301 may display similar options 291-296 as stage 204 of FIG. 2. As shown in stage 301, the option 291 may be selected to change the name of the beverage bottle. The name of the beverage container may be displayed on the UI 232 of the electronic device 235 and/or on the display 115 of the beverage container 101-103.

Figure 4:
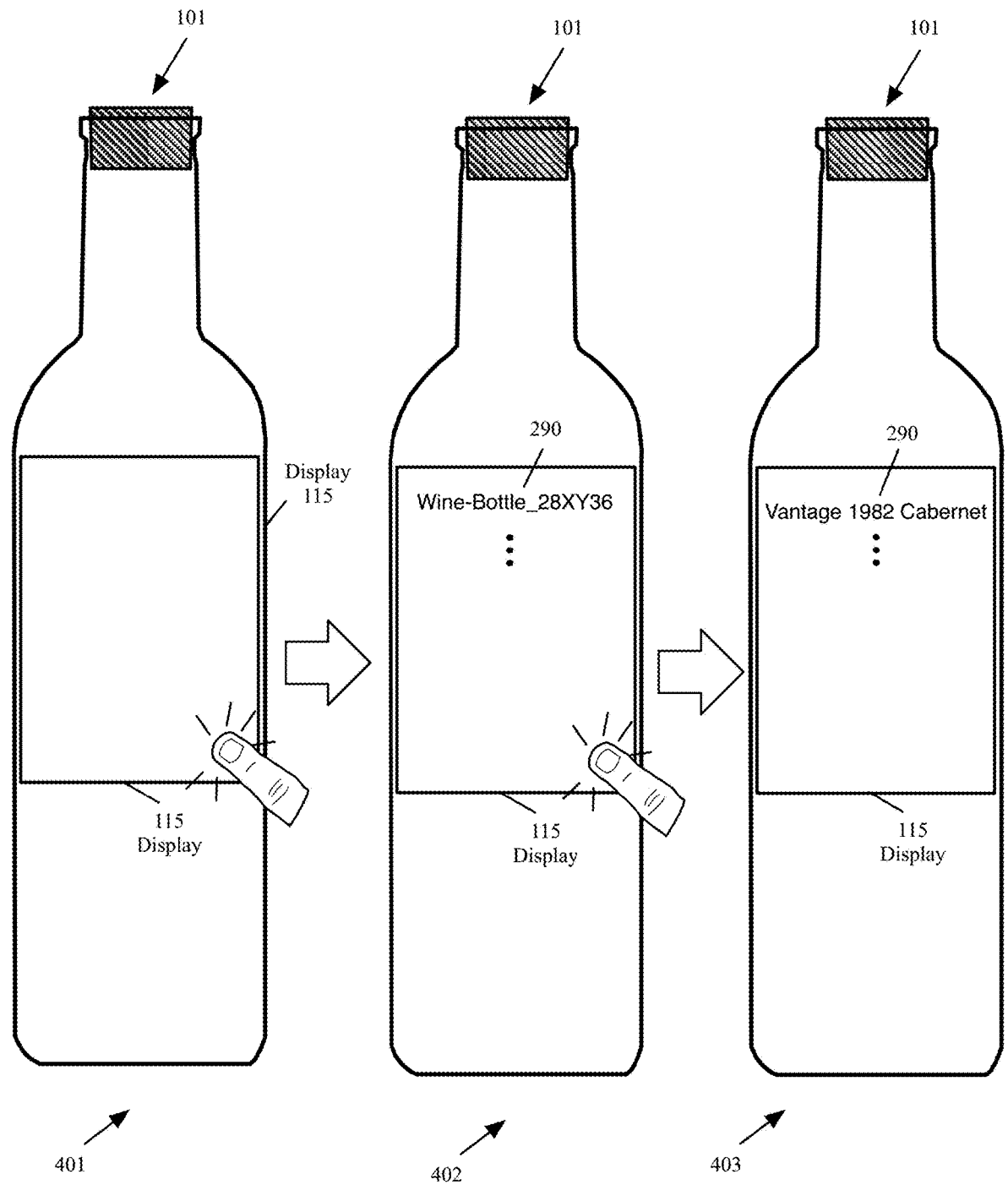
FIG. 4 is a schematic front view of a beverage container illustrating the name of a beverage container being changed by an external electronic device, according to various aspects of the present disclosure.

FIG. 4 is a schematic front view of a beverage container illustrating the name of the beverage container being changed by an external electronic device, according to various aspects of the present disclosure. Although the examples of FIGS. 2-9 are described with reference to a wine bottle 101, the same discussion regarding communication with external devices applies to any beverage container 101-103 of FIGS. 1A-1C, respectively.

The figure includes three stages 401-403. In stage 401, the display 115 of the beverage container 101 may be turned off. For example, in some embodiments, the display 115 may automatically turn off after a period of inactivity (e.g., a period where the beverage container's display is not touched, a period where the processor of the beverage container has not updated the display, and/or a period where the beverage container has not moved).

As shown in stage 401, the display 115 may be turned on, for example, by touching (or tapping) the display a number of times or by performing another type touch gesture. As shown in stage 402, the name of 290 of the beverage container is the same as the name 290 displayed on the UI 232 of the electronic device 235 in stage 301 of FIG. 3.

With reference to FIG. 3, the UI 232, in stage 302, may provide a display area 340 to display the beverage container's current name to allow the name to be edited. If the display 230 of the electronic device 235 is a touchscreen, a representation 350 of a keyboard may be displayed on the display 230 of the electronic device 235 to receive the user input. An indicator (e.g., a cursor point) 355 may identify the point that may be affected by an input from the user.

The UI 232, in stage 302, may display a message 320 to edit the name of the beverage container. The UI 232 may also provide an option 360 to save the name and an option 365 to cancel the changing of the name. As shown in the example of FIG. 3, the name of the beverage container is changed and the save option 360 is selected in stage 302.

In response, the UI 232, in stage 303, may update the name 290 of the beverage container. The electronic device 235 may send the updated name to the processor of the beverage container. As shown in stage 403 of FIG. 4, the name 290 of the beverage container is updated on the electronic display 115 of the beverage container 101. For example, the electronic device 235 of FIG. 3 may send the updated name to the processor of the beverage container 101, which may store the updated name and may update the name 290 on the display 115 of the beverage container 101.

Figure 5:
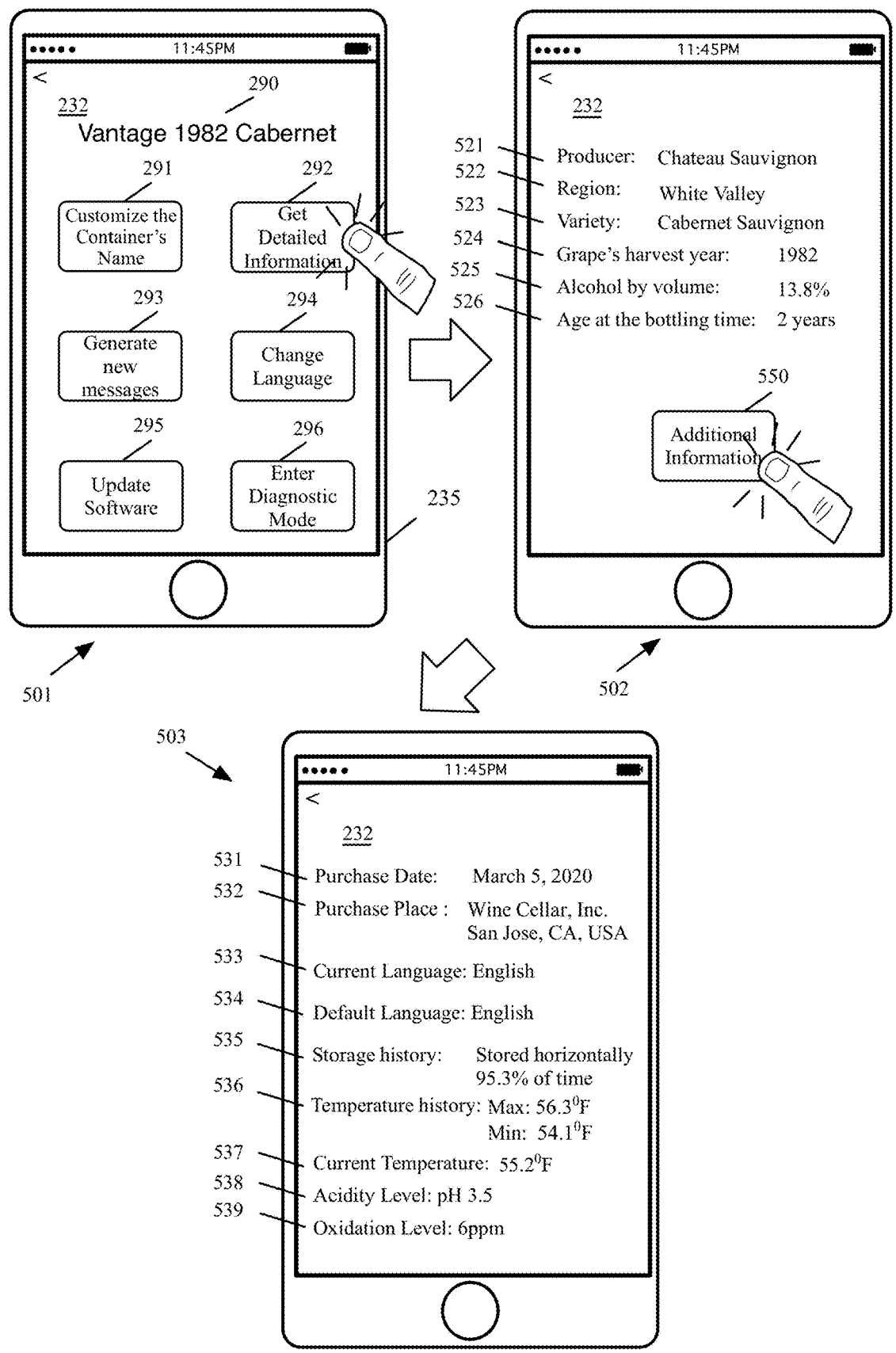
FIG. 5 illustrates a schematic front view of an electronic device that may include an application program for displaying the detailed information of a beverage container, according to various aspects of the present disclosure.

FIG. 5 illustrates a schematic front view of an electronic device that may include an application program for displaying the detailed information of a beverage container, according to various aspects of the present disclosure. The figure, as shown, includes three stages 501-503. Stage 501 may display similar options 291-296 as stage 204 of FIG. 2. As shown in stage 501, the option 292 may be selected to receive and display detailed information about the beverage container.

In response, the electronic device 235 may communicate with the beverage container 101-103 (FIGS. 1A-1C) and may receive information regarding the beverage container. The information may be stored on the memory 122 of the beverage container 101-103. The beverage container 101-103 may send the information to the electronic device 235 through the wireless transceiver(s) 124 (FIGS. 1A-1C) or through the NFC chip 125.

The UI 212, in stage 502, may display information regarding the beverage container. For the example wine bottle of FIG. 5, the information may include the producer's name 521, the region where the grape was grown (or the region where the wine was made) 522, the wine's variety 523, the grape's harvest year 524, the alcohol by volume of the wine at the bottling time 525, and/or the age of wine at the bottling time 526. In some embodiments, some or all the information 521-526 may be stored in permanent memory of the beverage container and may not be editable.

In stage 502, the option 550 may be selected to display additional information. In response, the UI 232, in stage 503, may display additional information 531-539 about the beverage container. For the example wine bottle of FIG. 5, the information may include the purchase date 531, the place of purchase 532, the current language 533 used to display messages, the default language 534, the storage history 535 of the wine bottle, the temperature history 536 of the wine bottle, the current temperature 536 of the interior of the wine bottle, the acidity level 538 of the wine, and/or the oxidation level 539 of the wine.

As described above, the magnetometer and/or the gyroscope of the beverage container may be used by the processor 121 to determine the orientation of the beverage container. The orientation of the beverage container may be used to determine whether the beverage container (e.g., the wine bottle 101 of FIG. 1A) is stored in an optimal position during long term storage. The storage history 535 of the wine bottle may be stored in the beverage container memory 122.

Figure 6A:
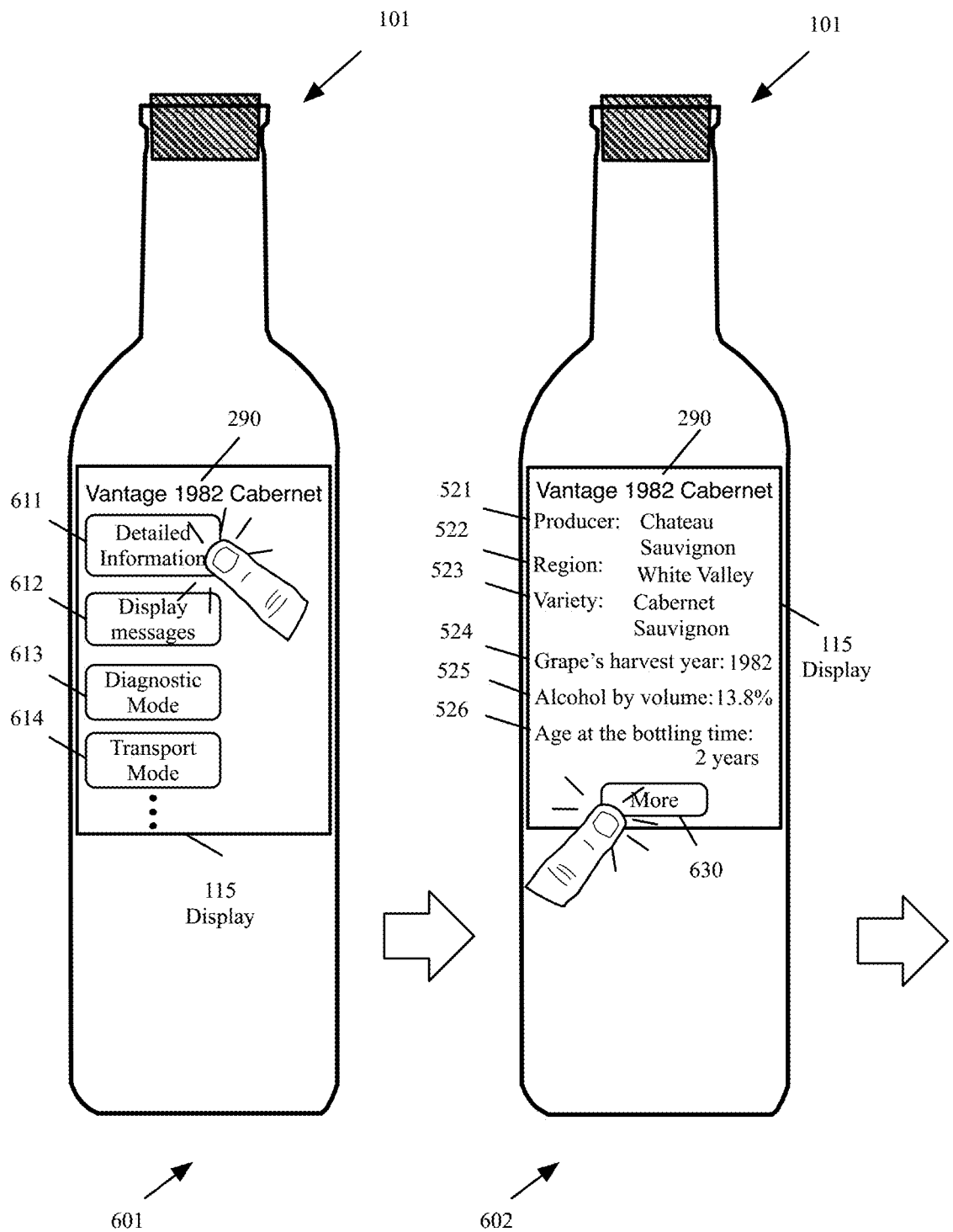
FIGS. 6A-6B illustrate a schematic front view of a beverage container that may display information regarding the contents of the beverage container, according to various aspects of the present disclosure.
Figure 6B:
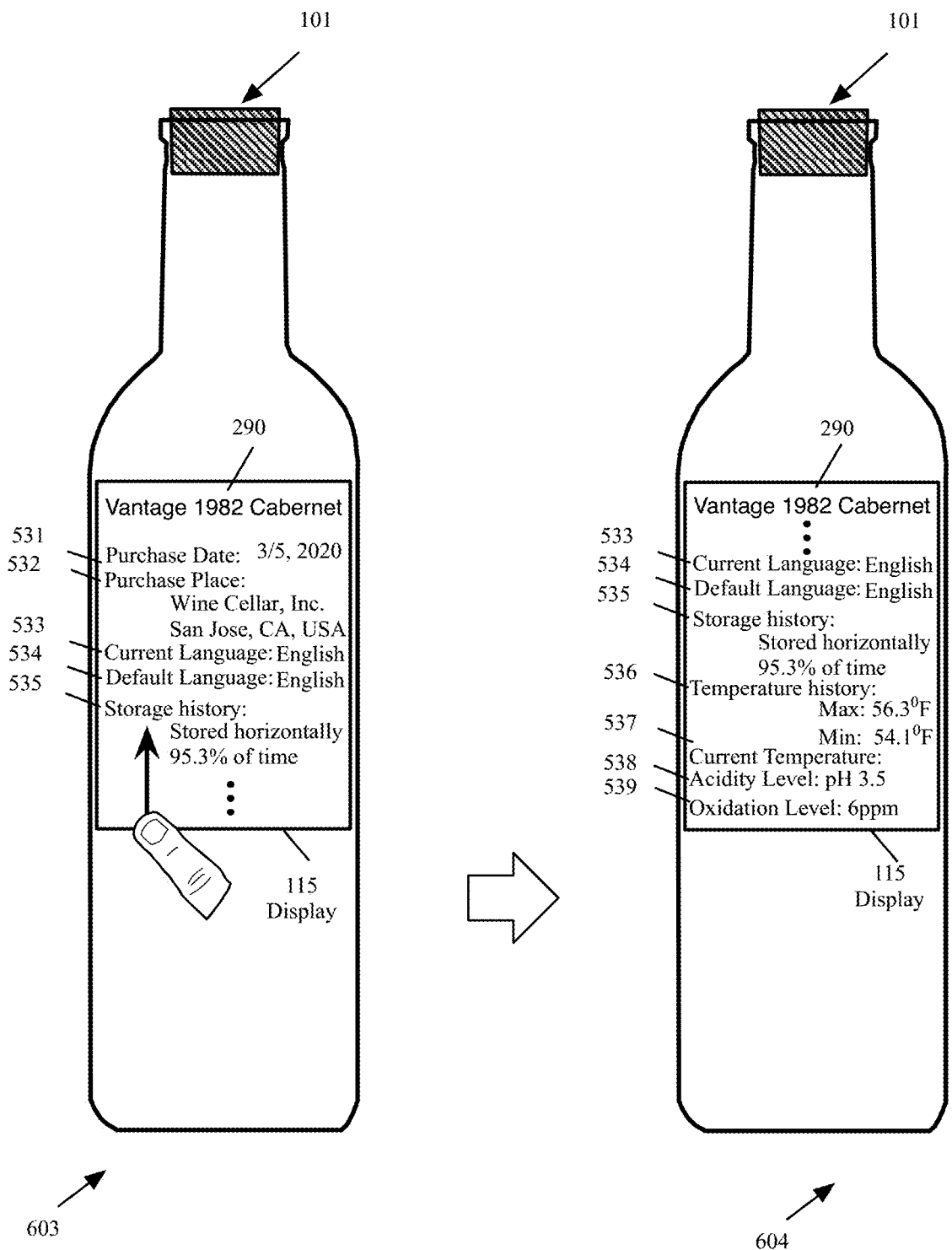

Similar information as the information 521-526 and 531-539 may be displayed on the display 115 of the beverage container 101-103. FIGS. 6A-6B illustrate a schematic front view of a beverage container that may display information regarding the contents of the beverage container, according to various aspects of the present disclosure. The figures include four stages 601-604. In stage 601, the display 115 of the beverage container 101 may display several options 611-614. As shown, the option 611 may be selected to display detailed information about the contents of the beverage container 101.

In response, the display 115, in stage 602, may display the information 521-526 regarding the beverage in the beverage container. The information 521-526 may be similar to the 521-526 described above with reference to FIG. 5. In stage 602, the option 630 may be selected to display additional information about the beverage.

In response, additional information 531-535 may be displayed on the display 115 of the beverage container 101 in stage 603. If all the information does not fit on the display, the user may perform a touch gesture (e.g., a drag gesture) on the display 115 in order to display the additional information. In response to receiving the touch gesture, the display 115, in stage 604, may display the additional information 536-539. The user may scroll the information up and down by performing additional gestures in up or down directions.

Figure 7:
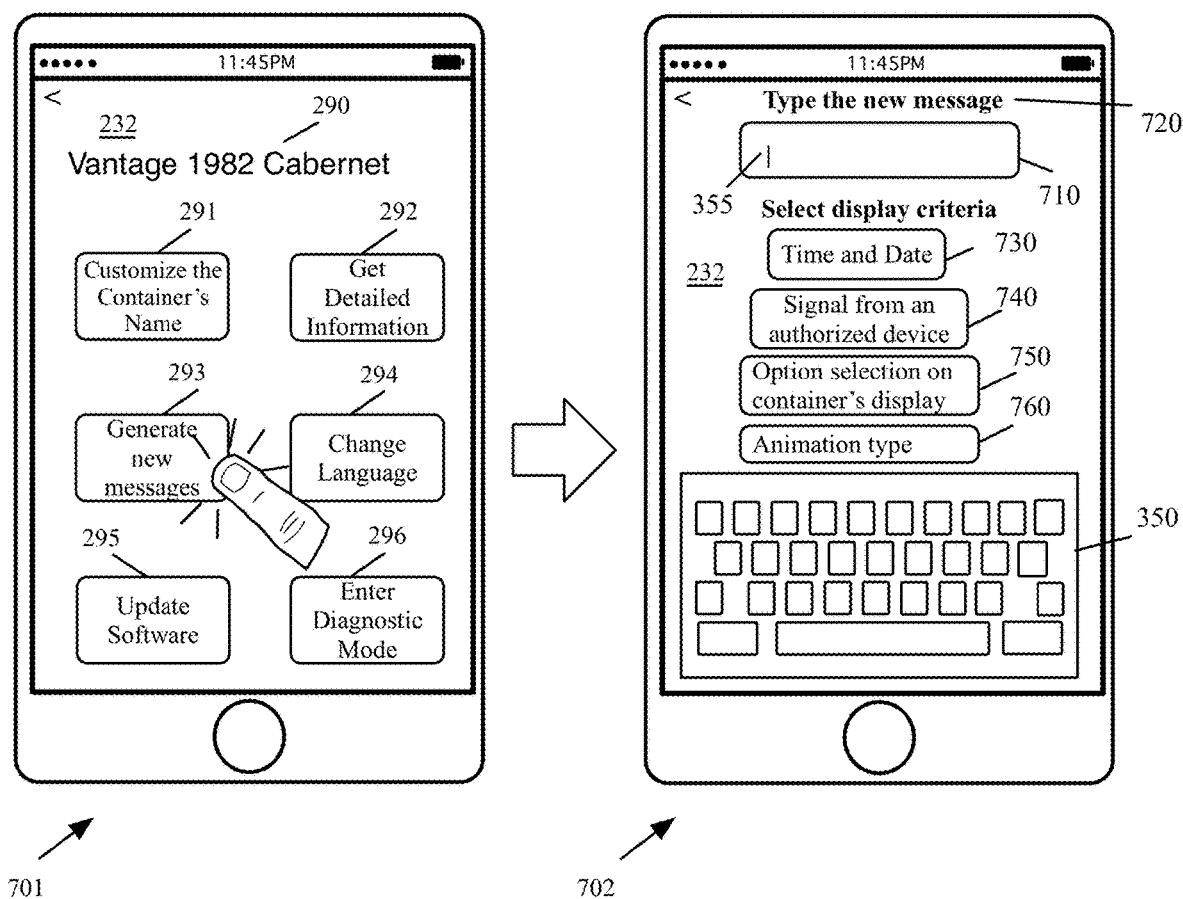
FIG. 7 illustrates a schematic front view of an electronic device that may include an application program for generating new messages to be displayed on the electronic display of a beverage container, according to various aspects of the present disclosure.

FIG. 7 illustrates a schematic front view of an electronic device that may include an application program for generating new messages to be displayed on the electronic display of a beverage container, according to various aspects of the present disclosure. The figure, as shown, includes two stages 701 and 702. Stage 701 may display similar options 291-296 as stage 204 of FIG. 2. As shown in stage 701, the option 293 may be selected to generate new messages to be displayed on the display 115 of the beverage container.

In response, the UI 232 may display a region 710 for typing a new message. If the display 230 of the electronic device 235 is a touchscreen, a representation 350 of a keyboard may be displayed on the display 230 of the electronic device 235 for receiving the user input. An indicator (e.g., a cursor point) 355 may identify the point that may be affected by an input from the user.

The UI 232 may display a message 720 for typing the new message. The UI 232 may provide the options 730-150 to determine one or more criteria for displaying the message. The option 730 may be used to indicate a time and date to display the message. The option 740 may be used to indicate that the message is to be displayed when the beverage container receives a signal from an authorized external device to display the message. The option 750 may be used to indicate that the message may be displayed when an option (e.g., the option 612 shown in stage 601 of FIG. 1) is selected on the display of the beverage container.

The UI 760 may provide an option 760 to select one or more types of animation to be played when the message is being displayed. For example, selecting the option 760 may provide a selection of different melodies that may be played and/or different animations that may be displayed with the message.

Figure 8:
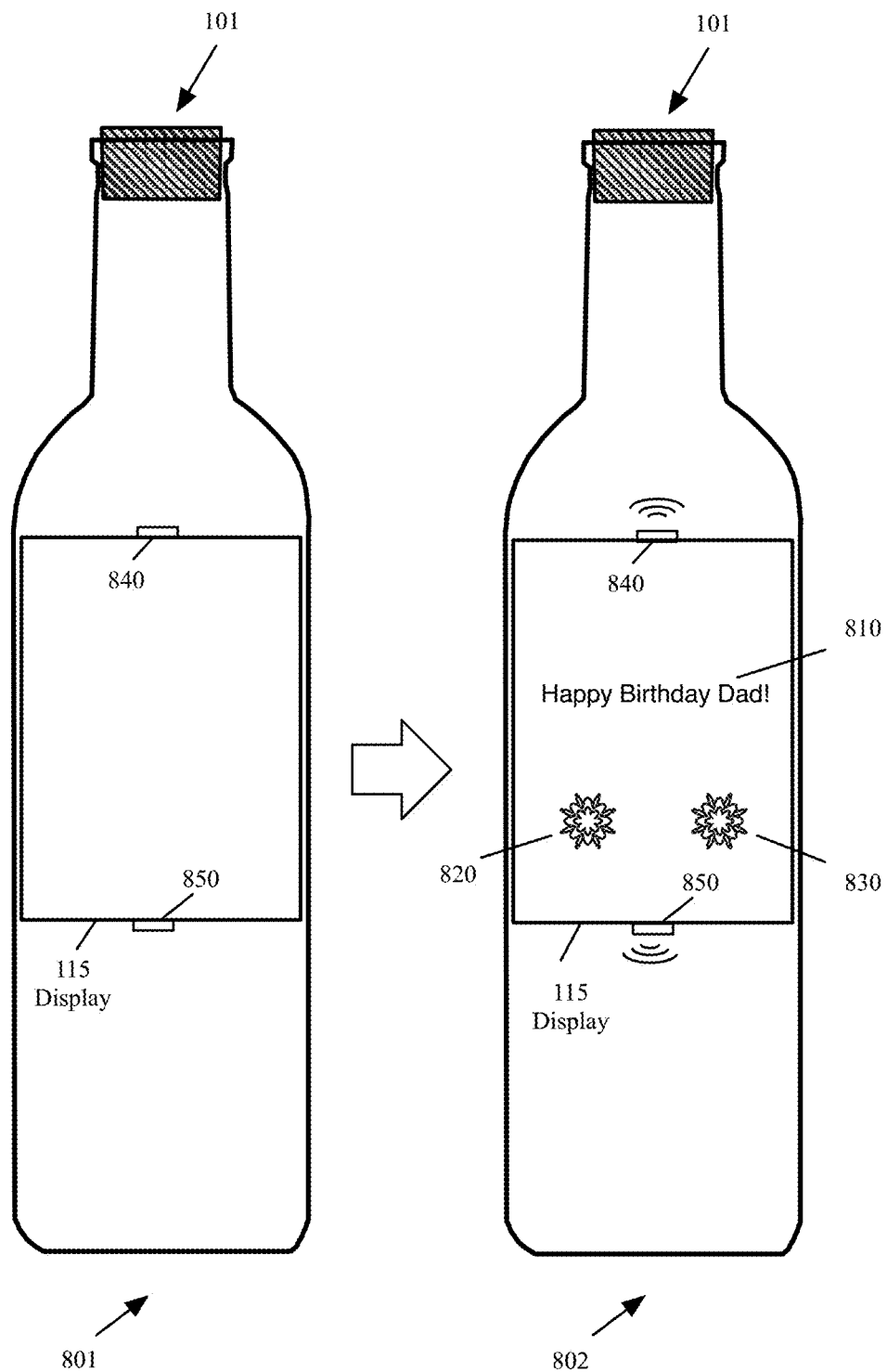
FIG. 8 illustrates a schematic front view of a beverage container illustrating a message being displayed on the electronic display of the beverage container, according to various aspects of the present disclosure.

FIG. 8 illustrates a schematic front view of a beverage container illustrating a message being displayed on the electronic display of the beverage container, according to various aspects of the present disclosure. The example of FIG. 8 assumes that a customized message has been generated using an interface similar to the UI 232 of FIG. 7. In this example, in addition to defining a message, the user has selected a particular time and date to display the message. The user has also selected one or more sound clips as well as display animation to be played with the message.

FIG. 8, as shown, includes two stages 801 and 802. In stage 801, the display 115 of the beverage container 101 may be turned off. In stage 802, the time specified to display the message may have arrived. The processor 121 (FIG. 1A) of the beverage container 101 may turn on the display 115 and may display the message 810 on the display 115 when the processor determines that the time to display the message is reached.

As shown, the beverage container may include one or more speakers 840-850. The speakers 840-850 may be, for example, and without limitations, small piezo electric speakers that may be attached to the display or to the outside of the beverage container 101. The processor 121 may have received one or more sound clips (e.g., one or more melodies) to be played with the message 810. The processor 121, in stage 802, may send digital notes to the speakers 840-850 to play. In addition, in the example of FIG. 8, the processor may display one or more animations 820-830 on the display 115. The processor 121 may receive and store the sound clips and the animations from an external electronic device, for example, when the option 293 is selected in stage 701 of FIG. 7.

Figure 9:
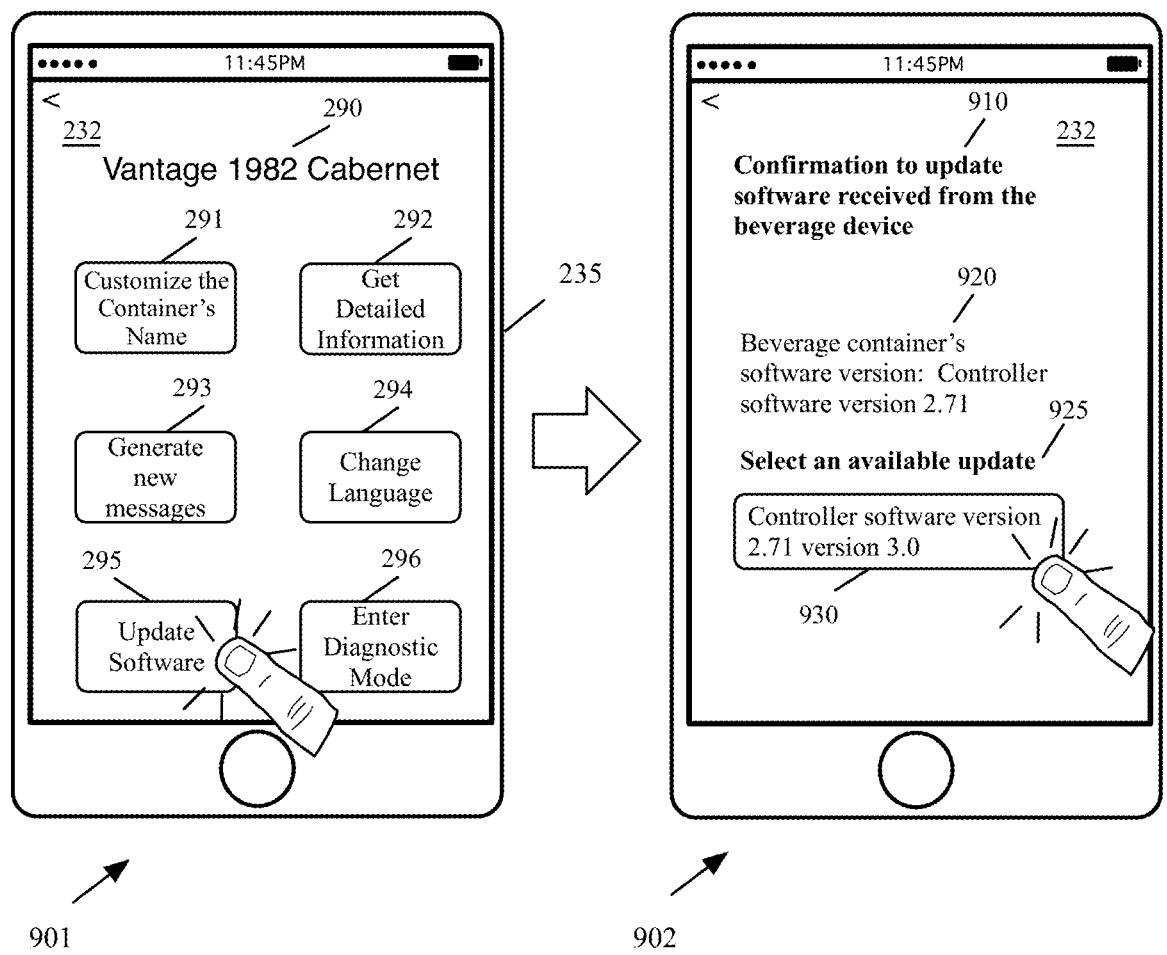
FIG. 9 illustrates a schematic front view of an electronic device that may include an application program for updating the software and/or the firmware of a beverage container, according to various aspects of the present disclosure.

FIG. 9 illustrates a schematic front view of an electronic device that may include an application program for updating the software and/or the firmware of a beverage container, according to various aspects of the present disclosure. The figure includes two stages 901 and 902. Stage 901 may display similar options 291-296 as stage 204 of FIG. 2. As shown in stage 901, the option to update software (and/or firmware) 295 may be selected.

In response, the UI 232, in stage 902, may display a message 910 indicating that a confirmation is received from the beverage container to update the software or firmware.

For example, in some embodiments, an electronic device that is authenticated to communicate with a beverage container may send a request to update the beverage container's software or firmware. The beverage container may authorize the authenticated electronic device to download the software or firmware through an established connection such as wireless or NFC. Some embodiments may display a message on the beverage container's display and may request a user to manually confirm the request to update the software or the firmware.

As shown in stage 902, the current software version 920 of the beverage container may be displayed. For example, the electronic device may receive the current software version from the processor of the beverage container. The UI 232 may display a message 925 to select an available update and may display the available software updates 930 (in this example only one update is available). The available updates may depend on the current version of the software already loaded in the beverage container and/or on the type of the beverage container (e.g., a bottle, a can, etc.). As shown, in the option 930 may be selected in stage 902. In response, the software update may be downloaded from the electronic device 235 into the beverage container.

III. Recharging the Battery

The battery 123 of the beverage container, in some embodiments, may be a rechargeable battery. The processor 121, in some embodiments, may measure the charge level of the battery 123. The processor 121, in some embodiments, may display one or more messages on the display 115 and/or may send one or more signals to one or more authorized external devices to indicate the charge level of the battery, to indicate that the battery requires recharging (e.g., when the charge level is below a first threshold), and/or to indicate that the battery is charged (e.g., when the charge level is above a second threshold).

Figure 10A:
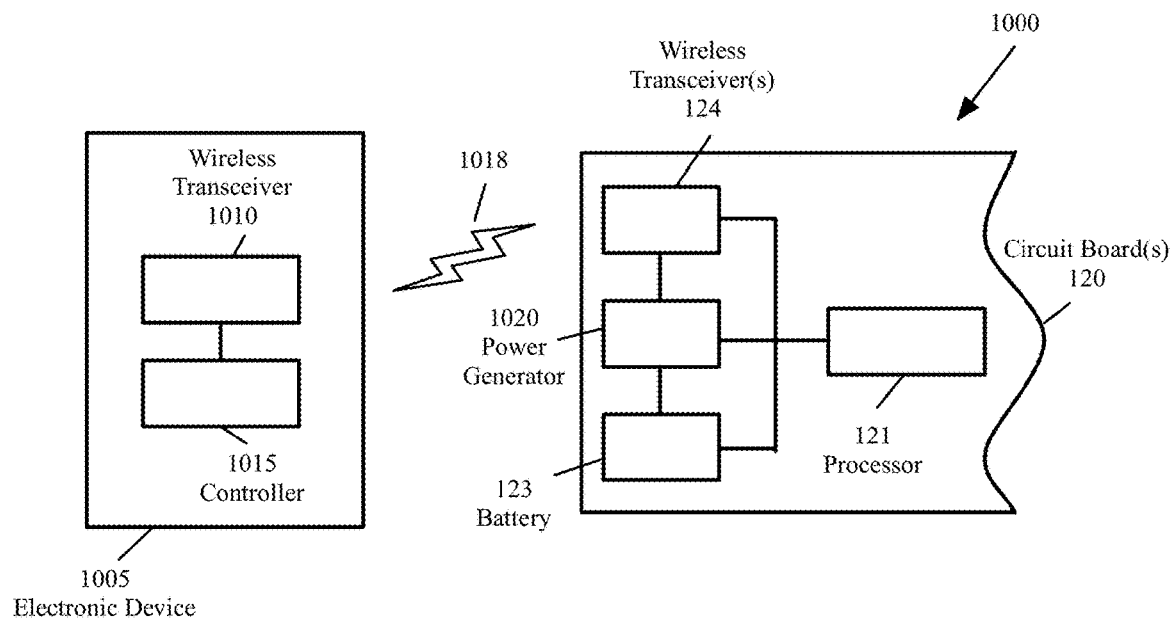
FIG. 10A is a functional block diagram illustrating a portion of an example system for charging a battery of a beverage container through a wireless channel, according to various embodiments of the present disclosure.

The battery, in some embodiments, may be charged by wireless radio signals. FIG. 10A is a functional block diagram illustrating a portion of an example system for charging a battery of a beverage container through a wireless channel, according to various embodiments of the present disclosure. FIG. 10A shows a portion of the circuit board(s) 120 of a beverage container 1000, which may be any one of the beverage containers 101-103 of FIGS. 1A-1C, respectively. In addition to the processor 121, the battery 123, and the wireless transceiver(s) 124 that were described above, the circuit board(s) 120 of FIG. 10A may include a power generator 1020.

With reference to FIG. 10A, the electronic device 1005 may be a smartphone, a desktop computer, a laptop computer, a tablet, etc. The beverage container 1000 may receive wireless signals 1018, through at least one of the wireless transceiver(s) 124, from the wireless transceiver 1010 of the electronic device 1005. The energy received by the wireless transceiver 124 may be converted to a voltage (or current) by the power generator 1020 that may be used to charge the battery 123.

The processor 121 of the beverage container may be configured to control whether or not the power generator 1020 may charge the battery 123. In some embodiments, the electronic device 1005 may include a controller 1015 (e.g., a processor) that may establish communication with the beverage container 1000 through a wireless communication channel. In other embodiments, the power generator may operate as a power scavenger. In these embodiments, the wireless transceiver(s) 124 of the beverage container 1000 may receive wireless signals 128 from the environment and the power generator 1020 may use the received energy to charge the battery 123. Some embodiments may use a standard, such as, for example, and without limitations, the Qi wireless charging standard to recharge the battery 123.

Figure 10B:
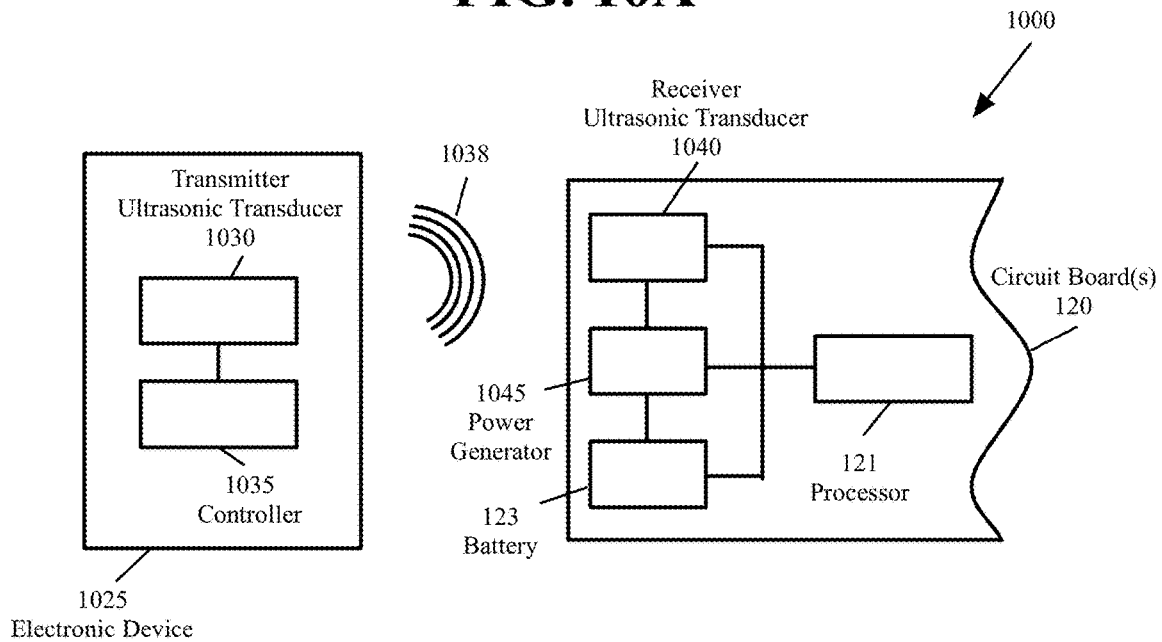
FIG. 10B is a functional block diagram illustrating a portion of an example system for charging a battery of a beverage container using ultrasound, according to various embodiments of the present disclosure.

The battery, in some embodiments, may be charged by ultrasound waves. FIG. 10B is a functional block diagram illustrating a portion of an example system for charging a battery of a beverage container using ultrasound, according to various embodiments of the present disclosure. FIG. 10B shows a portion of the circuit board(s) 120 of a beverage container 1000, which may be any one of the beverage containers 101-103 of FIGS. 1A-1C. In addition to the processor 121 and the battery 123 that were described above, the circuit board(s) 120 of FIG. 10B may include a receiver ultrasonic transducer 1040 and a power generator 1045.

With reference to FIG. 10B, the electronic device 1025 may include a controller 1035 (e.g., a processor) and a transmitter ultrasonic transducer 1030. The receiver ultrasonic transducer 1040 may receive ultrasonic waves 1038, from the transmitter ultrasonic transducer 1030 of the electronic device 1025. The energy received by the receiver ultrasonic transducer 1040 may be converted to a voltage (or current) by the power generator 1045 that may be used to charge the battery 123. The processor 121 may be configured to control whether or not the power generator 1045 may charge the battery 123.

Figure 10C:
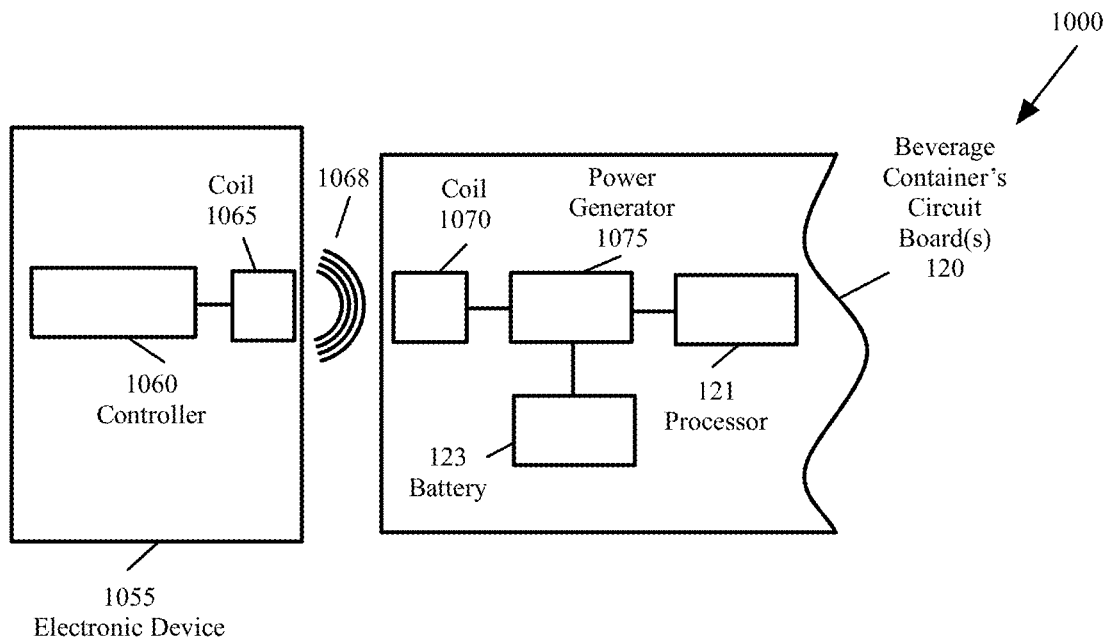
FIG. 10C is a functional block diagram illustrating a portion of an example system for charging a battery of a beverage container using an electromagnetic coil, according to various embodiments of the present disclosure.

The battery, in some embodiments, may be charged through electromagnetic inductive charging. FIG. 10C is a functional block diagram illustrating a portion of an example system for charging a battery of a beverage container using an electromagnetic coil, according to various embodiments of the present disclosure. FIG. 10C shows a portion of the circuit board(s) 120 of a beverage container 1000, which may be any one of the beverage containers 101-103 of FIGS. 1A-1C. In addition to the processor 121 and the battery 123 that were described above, the circuit board(s) 120 of FIG. 10C may include a coil 1070 and a power generator 1075.

With reference to FIG. 10C, the electronic device 1055 and the beverage container 1000 may be placed in the vicinity of each other. The coil 1065, in some embodiments, may be in a charging pad (not shown). In these embodiments, the beverage container 1000 may be placed over the charging pad.

The electronic device 1055 may include a controller 1060 and the coil 1065. The controller 1060 may provide alternating voltage to the coil 1065, causing the coil 1065 to generate an electromagnetic field 1068. The electromagnetic energy received by the coil 1070 may be converted to a voltage (or current) that may be used by the power generator 1075 to charge the battery 123. The processor 121 may be configured to control whether or not the power generator 1075 may charge the battery 123.

Figure 10D:
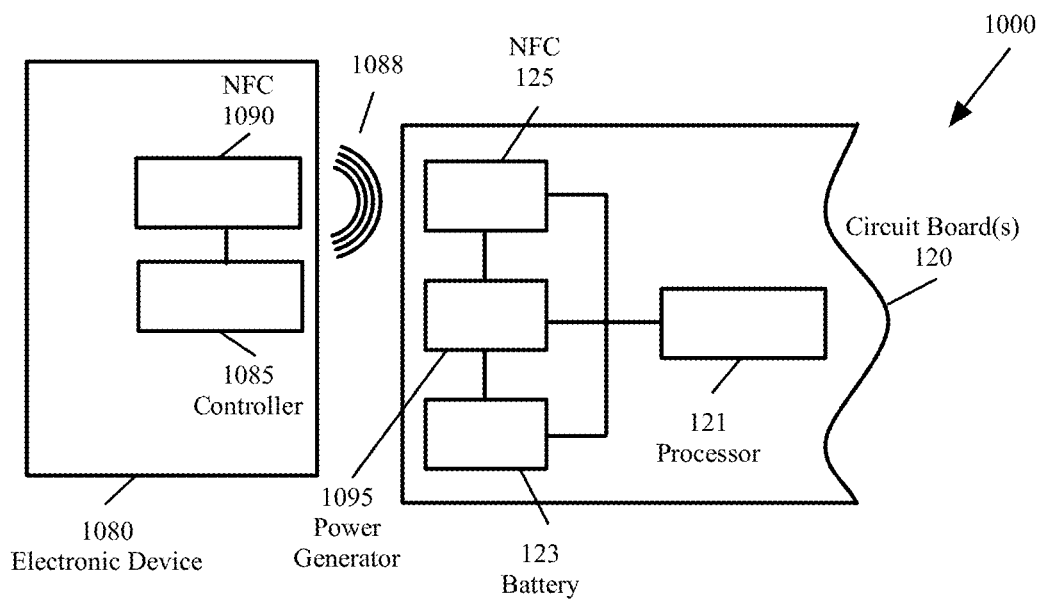
FIG. 10D is a functional block diagram illustrating a portion of an example system for charging a battery of a beverage container using a near field communication (NFC) chip, according to various embodiments of the present disclosure.

FIG. 10D is a functional block diagram illustrating a portion of an example system for charging a battery of a beverage container using an NFC chip, according to various embodiments of the present disclosure. FIG. 10D shows a portion of the circuit board(s) 120 of a beverage container 1000, which may be any one of the beverage containers 101-103 of FIGS. 1A-1C. In addition to the processor 121, the battery 123, and the NFC chip 125 that were described above, the circuit board(s) 120 of FIG. 10D may include a power generator 1095.

The electronic device 1080 may be a smartphone, a desktop computer, a laptop computer, a tablet, etc. The electronic device 1080 and the beverage container 1000 may be placed in the vicinity of each other. The electronic device 1080 may include a controller 1085 and an NFC chip 1090. The controller 1085 and the processor 121 may configure the NFC chips 1090 and 125, respectively to couple with each other. The electromagnetic energy received by the NFC chip 125 may be converted to a voltage (or current) that may be used by the power generator 1095 to charge the battery 123.

In some embodiments, the beverage container 101-103 may include a seal 140 that is made of a material that may allow a USB port to be attached to the seal. The seal 140, in some embodiments, may be used to hold a USB port for charging the beverage container's battery.

Figure 11A:
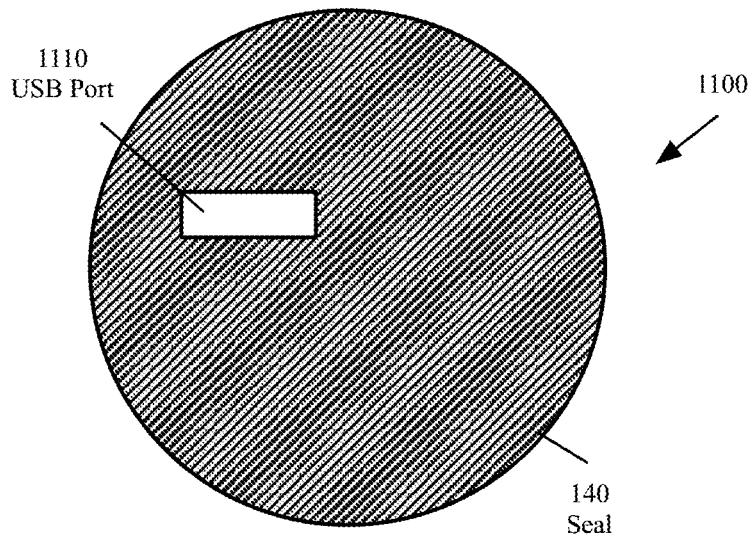
FIG. 11A is a bottom view of the seal at the bottom of a beverage container that may include a USB port, according to various aspects of the present disclosure.
Figure 11B:
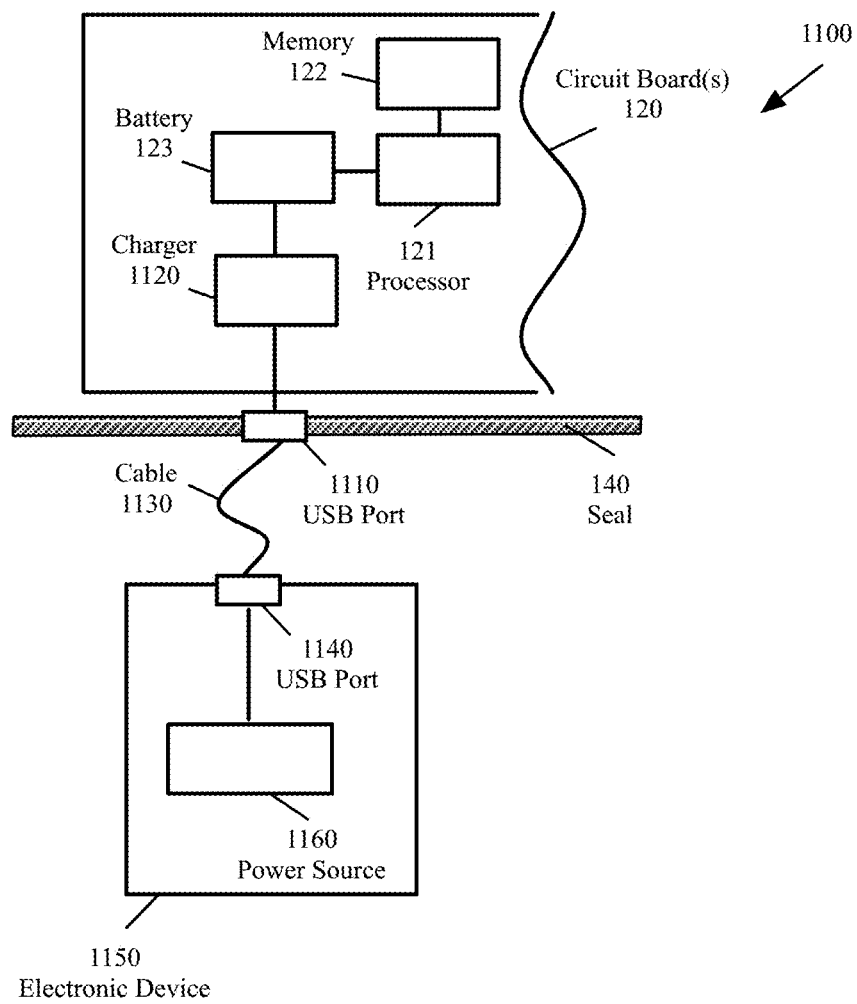
FIG. 11B is a functional block diagram illustrating a portion of an example system for charging the battery of a beverage container using a USB port, according to various embodiments of the present disclosure.

FIG. 11A is a bottom view of the seal at the bottom of a beverage container 1100 that may include a USB port 1110, according to various aspects of the present disclosure. FIG. 11B is a functional block diagram illustrating a portion of an example system for charging the battery of a beverage container using a USB port, according to various embodiments of the present disclosure. The beverage container 1100 may be similar to any of the beverage containers 101-103 of FIGS. 1A-1C, described above.

With reference to FIG. 11A, the USB port 1110 may be embedded in the seal 140. The USB port may be, for example, and without limitations, Type-A, Type-B, Type-C, Mini-USB, or Micro-USB. With reference to FIG. 11B, the USB port 123 may be connected by a cable 1130 to a USB port 1140 of an electronic device 1150 and may receive power from the USB port 1140. The electronic device 1150 may be, for example, and without limitations, as a laptop, a desktop, a smartphone, etc., that may include a power source 1160 such as a battery. The power source 1160 may be connected to the USB port 1140. The charger 1120 may receive power from the USB port 1110 and may charge the battery 123. The processor 121 may be configured to control whether or not the charger 1120 may charge the battery 123.

In addition to, or in lieu of, receiving power from the USB port 1110, the beverage container 1100 may receive software and/or firmware updates, new messages (e.g., messages customized for an event, advertisements, etc.) from the electronic device 1150. The processor 121 of the beverage container 1100 may store the software and/or firmware updates, the new messages etc., in the memory 122 of the beverage container 1100. In some embodiments, the electronic device 1150 and a user interface, such as the user interface 232 of FIG. 5 may be used to perform diagnostics on the beverage container 1100 through the USB port 1110.

IV. Accessing the Beverage in the Container

The beverage compartment 105-107 of the beverage containers 101-103 may be filled with beverage at a bottling company, at a winery, etc. The beverage compartment 105-107 may then be closed until a consumer may open the beverage compartment. Depending on the type of the beverage and the type of the container, some embodiments may provide information such as whether or not the container has been opened (e.g., in case of a bottle of wine), whether it is safe to open the container (e.g., when the container include carbonated beverage), whether the cork will pop up (e.g., in case of a bottle of champagne), etc.

A. Determining Whether Beverage Container's Cork has been Removed

Figure 12A:
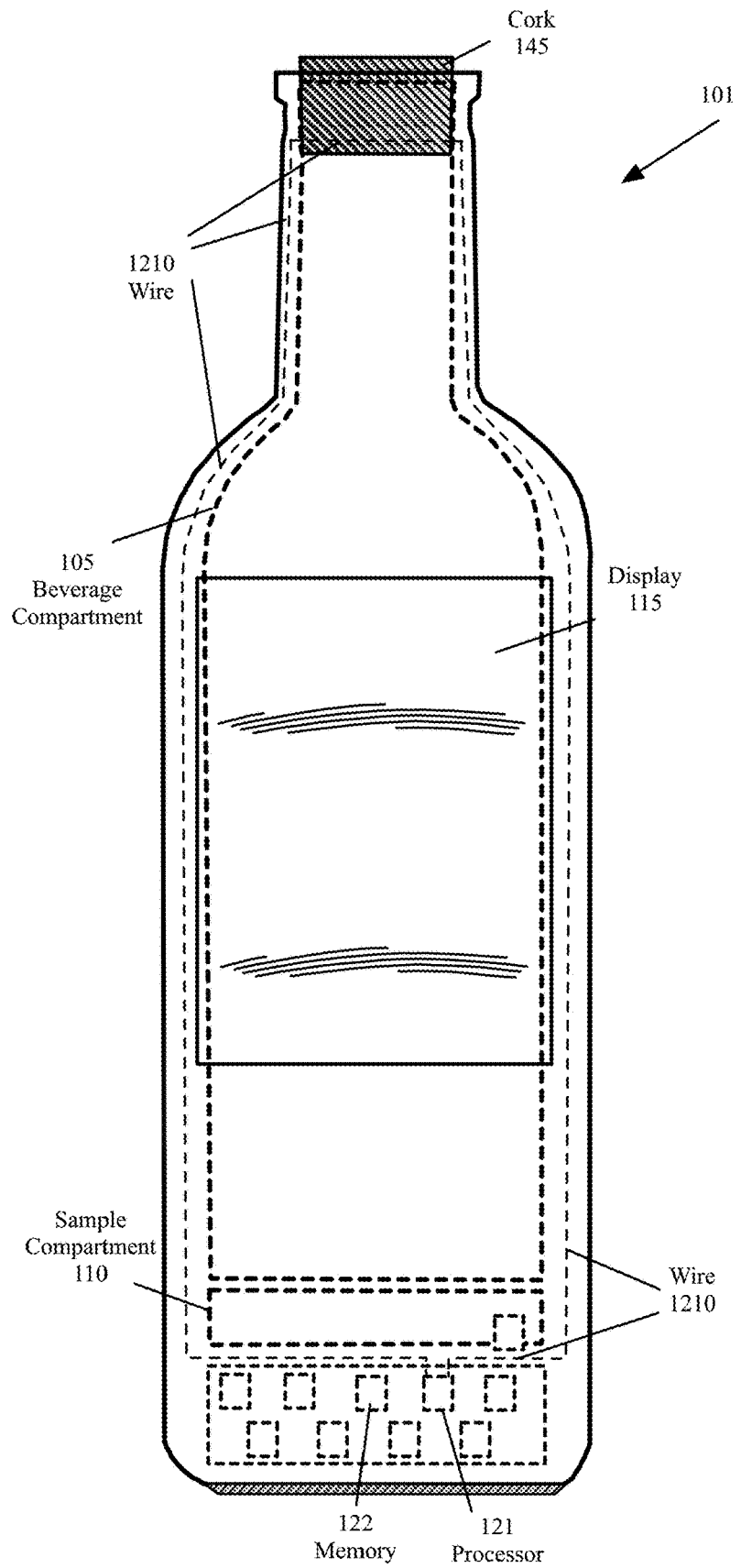
FIG. 12A is a functional block diagram illustrating an example system for determining whether a beverage container has been opened by using a set of wires, according to various embodiments of the present disclosure.
Figure 12B:
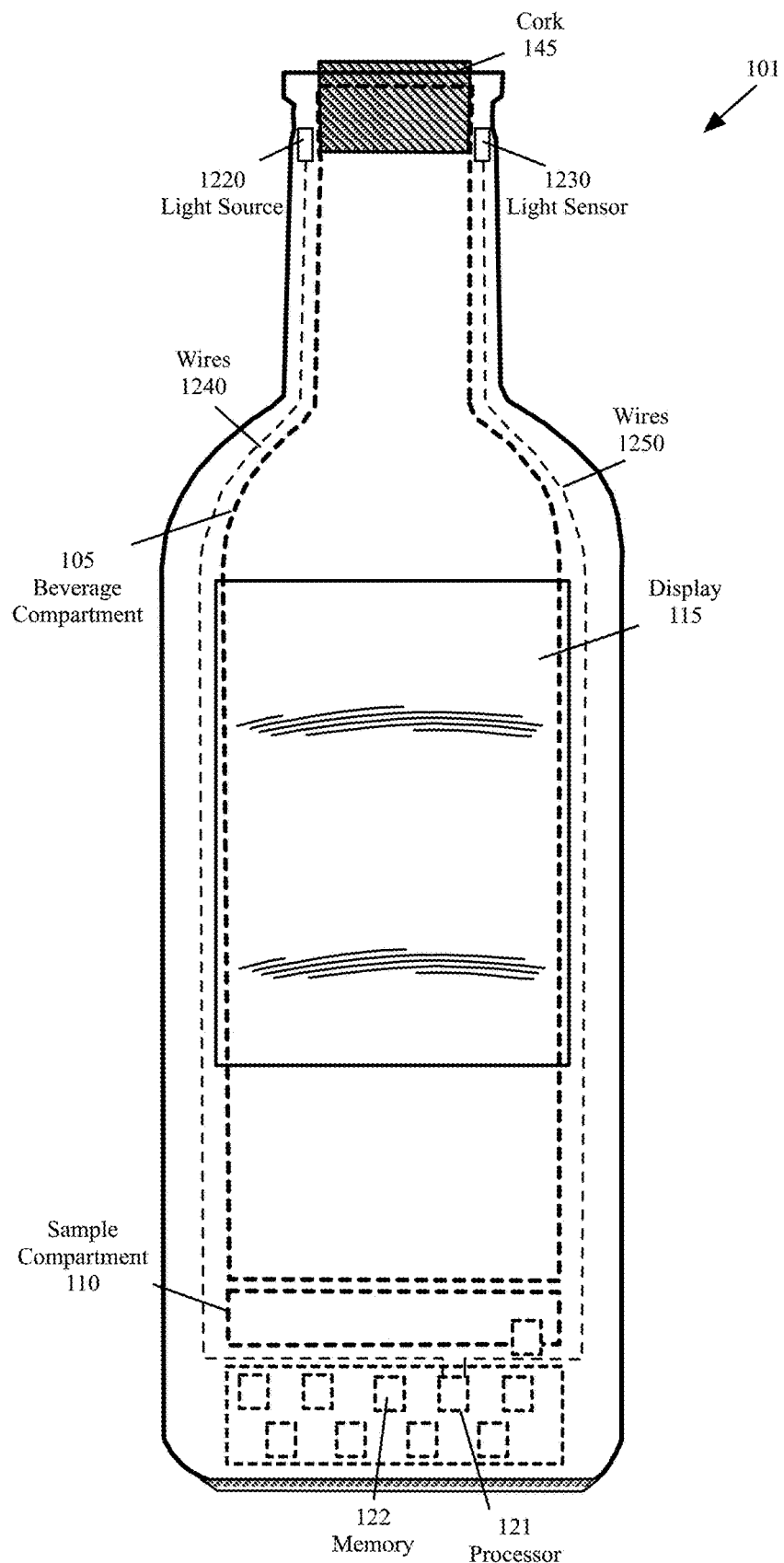
FIG. 12B is a functional block diagram illustrating an example system for determining whether a beverage container has been opened by using a light source and a light sensor, according to various embodiments of the present disclosure.

FIG. 12A is a functional block diagram illustrating an example system for determining whether a beverage container has been opened by using a set of wires, according to various embodiments of the present disclosure. FIG. 12B is a functional block diagram illustrating an example system for determining whether a beverage container has been opened by using a light source and a light sensor, according to various embodiments of the present disclosure.

It is well known that once a wine bottle is opened, the contents have to be consumed in a few days otherwise the contents may change to vinegar or otherwise may not be palpable. In addition, it is desirable to know whether the contents of an expensive bottle of wine are original or have been replaced at a later time by a less expensive wine.

With reference to FIG. 12A, a wire 1210 may run through the cork 145 and may be connected to the processor 121 to make a closed electrical loop. The wire 1210 may be configured to have a length and strength such that when the cork 145 is pulled out of the bottle 101, the wire 1210 may break. Once the wire 1210 is broken, the loop made with the processor 121 is broken and the processor 121 may store one or more signals (e.g., one or more flags or one or more messages) in the permanent memory 122 of the beverage container 101, indicating that the cork has been opened. The processor 121 may also store the time and date of the opening of the cork. The processor 121 may display one or more signals or messages on the display 115 and/or may send one or more signals or messages to one or more authorized external electronic devices to indicate whether or not the cork has been opened.

With reference to FIG. 12B, the beverage container 101 may include a light source 1220 and a light sensor 1230 on the opposite sides of the cork 145. The light source 1220 may be, for example, and without limitations, an IR light source, a light emitting diode (LED), a laser light source, or other type of low powered light sources. The light sensor 1220 and the light sensor 1230 may be connected by a set of wires 1240 and 1250, respectively, to the processor 121 to receive power and/or to send data.

The light source 1220 may be configured to emit a light beam towards the light sensor 1230. As long as the cork 145 is in place, the light sensor 1230 may not receive light from the light source 1220. When the cork 145 is removed, the light sensor 1230 may receive light from the light source 1220. In response to receiving the light, the light sensor 1230 may send one or more signals to the processor 121 to indicate that the cork 145 is removed.

When the processor 121 receives the indication that the cork 145 is removed, the processor 121 may store one or more signals (e.g., one or more flags or one or more messages) in permanent memory 122 of the beverage container 101, indicating that the cork has been opened. The processor 121 may also store the time and date of the opening of the cork. The processor 121 may display one or more signals or messages on the display 115 and/or may send one or more signals or messages to one or more authorized external devices to indicate whether or not the cork has been opened.

Although FIGS. 12A and 12B are described with reference to a wine bottle, a similar configuration may be used to ensure that a bottle of liquor (e.g., cognac, brandy, champagne) has not been opened and the original contents replaced by a different (probably less expensive) liquor.

B. Estimating the Pressure of Undissolved Gas in the Beverage Compartment

The beverage compartments are typically filled such that the beverage does not completely fill the beverage compartment. Carbonated drinks have dissolved carbon dioxide ($CO_2$). Under the atmospheric pressure, $CO_2$ is a gas. When carbonated drinks are filled in the container, $CO_2$ is dissolved in the liquid beverage under pressure and the beverage container is sealed. After the beverage container is sealed, an equilibrium is made between the $CO_2$ that is dissolved in the liquid and the $CO_2$ that is trapped in the air above the liquid inside the beverage compartment.

Shaking of the beverage container may release the carbon dioxide ($CO_2$) from the beverage into the empty space in the beverage compartment. Opening the beverage compartment's cork 146 (FIG. 1B) or breaking the tab 148 (FIG. 1C) may cause the carbonated beverage to spill out of the beverage compartment. If the shaking stops and the beverage container remains unopened, the high pressure causes the released CO2 to dissolve back into the beverage until an equilibrium is made again between the dissolved gas and the gas above the liquid. The more vigorous the shaking, the farther away the gas goes from the equilibrium, and the more time is needed for the gas to get dissolved back in the beverage.

Some embodiments may determine whether opening a carbonated beverage container may cause the beverage to spill out after the beverage container has been shaken. Some embodiments may measure the amount of shaking and the time period after the shaking has stopped and compare them with experimental results for the same beverage and the same type of container to determine whether the beverage may spill out if the beverage container is opened. A message may be displayed on the display of the beverage container, if opening the beverage container may result in spilling the beverage out.

The amount of shaking, in some embodiments, may be measured by an accelerometer. The accelerometer may be a component of the IMU 128 (FIGS. 1A-1C) or may be on a separate IC chip. In some embodiments, a series of experiments may be performed. In each experiment, a can or a bottle of carbonated beverage may be shaken to create a predetermined amount of acceleration for a predetermined time period. The can or the bottle is let to rest for a period of time and is then opened. A determination may be made whether or not the beverage spills out. The determination, in some embodiments, may be made by a sensor placed outside the opening of the beverage container to detect any spilled liquid. The determination, in some embodiments, may be visually made by a person. For the same type of container, the same type of beverage, the same acceleration, and the same acceleration period, a can or bottle may be opened after different rest periods until a rest period is found that does not cause the beverage to spill out after opening.

Figure 13:
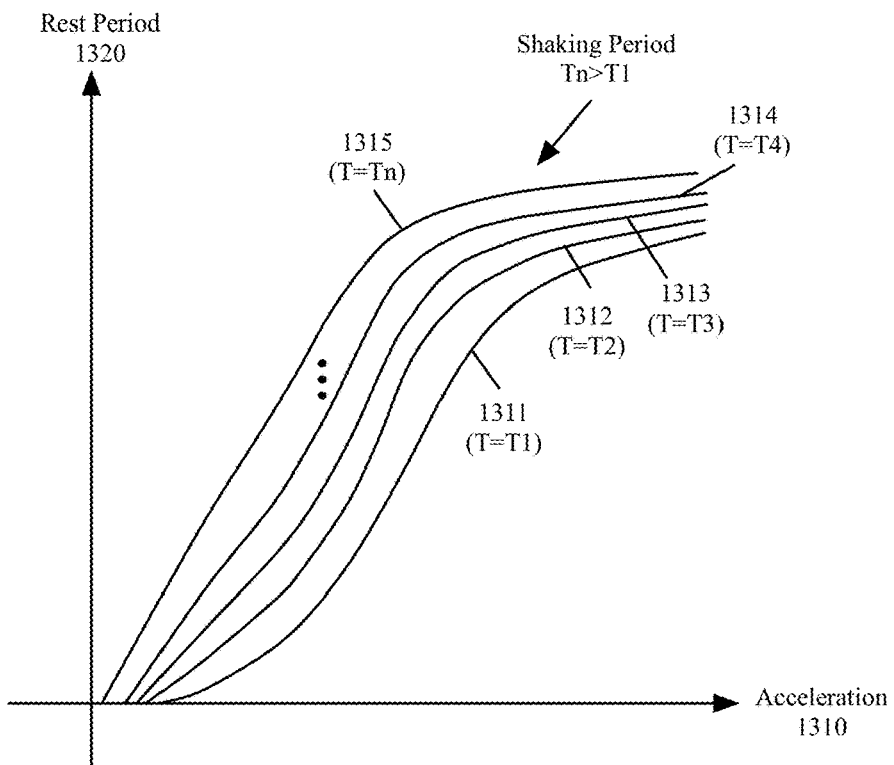
FIG. 13 illustrates an example set of the experimental curves that show the required rest periods to avoid beverage spilling for different accelerations values and different shaking periods, according to various aspects of the present disclosure.

The experiments may then be repeated with the same type of container and the same type of beverage with different accelerations and/or different shaking periods. The results may be stored in one or more tables. FIG. 13 illustrates an example set of the experimental curves that show the required rest periods 1320 to avoid beverage spilling for different accelerations values 1310 and different shaking periods, according to various aspects of the present disclosure. With reference to FIG. 13, the curves 1301-1305 may be drawn from a table generated from experimentation. All curves 1301-1305 are for the same size (e.g., 355 milliliter, 1 liter, 2 liters, etc.) of beverage container, the same type of beverage container (e.g., can, plastic bottle, glass bottle, etc.), and the same type of beverage (e.g., beer, regular soda, diet soda, etc.).

For example, the curves 1301-1305 in FIG. 13 may be drawn from the data collected from experiments made for a 355-milliliter aluminum can of regular (i.e., non-diet) soda. For each other beverage container size, beverage container type, and beverage type similar experiments may performed and the results may be stored in the form of tables in the memory of the associated containers.

With further reference to FIG. 13, each of the curves 1301-1305 is drawn for a constant shaking period T, for example, 1 second, 5 seconds, 10 seconds, etc. The values of acceleration and rest period associated with each curve may be stored in a separate table. In operation, when a beverage container 101-103 (FIGS. 1A-1C) is shaken, the accelerometer of the beverage container 101-103 (either the accelerometer in the IMU 128 or a separate accelerometer sensor) may measure the amount of acceleration generated during shaking.

During operation, the processor 121 of the beverage container may receive the accelerometer reading and may start measuring time when the accelerometer reading exceeds a threshold. Once the shaking stops, the processor 121 may use the amount of acceleration and the shaking duration to determine a rest period that is required before opening the beverage container to avoid spilling.

Figure 14:
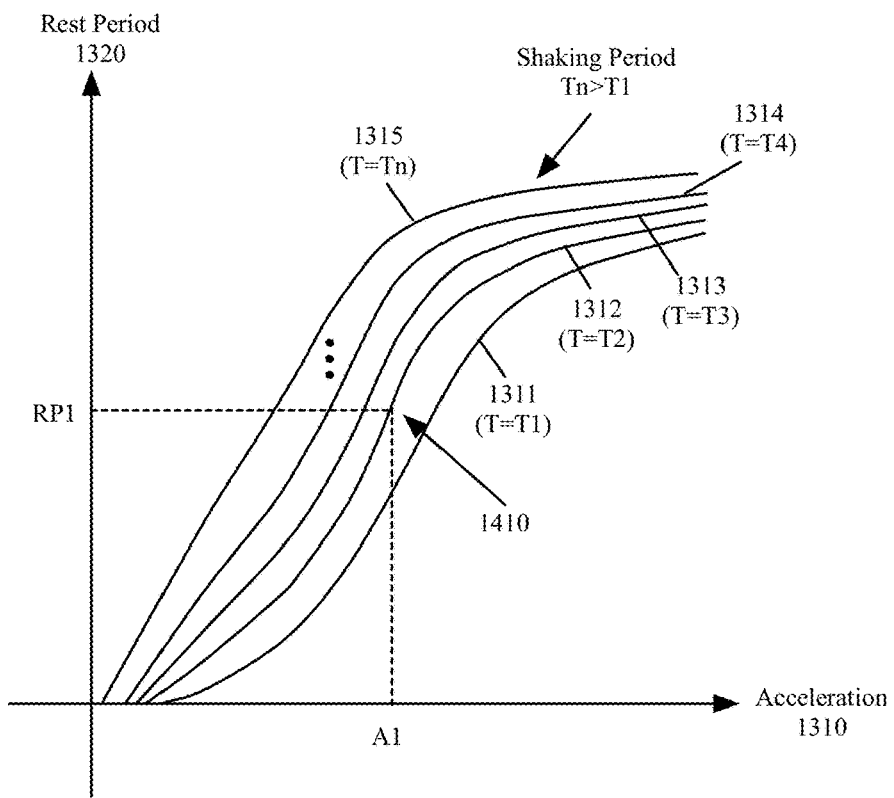
FIG. 14 illustrates an example use of the curves of FIG. 13 to determine whether opening a carbonated beverage can may result in spilling of the beverage, according to various aspects of the present disclosure.

FIG. 14 illustrates an example use of the curves of FIG. 13 to determine whether opening a carbonated beverage can may result in spilling of the beverage, according to various aspects of the present disclosure. With reference to FIG. 14, the processor 121 may have received an acceleration reading of A1 meters pers square seconds from the accelerometer of the beverage container for a period of T2 seconds. By mapping the A1 value to the point 1410 on the curve 1312 and finding the corresponding rest period RP1 on the rest period axis 1320, the processor may determine that a rest period of RP1 seconds may be needed to allow the CO2 gas in the beverage container to dissolve back in the beverage. Instead of using the curves 1311-1355, the processor 121 may use a table lookup. When the value of the shake period, T is not found in the table, an interpolation or an extrapolation may be made between the closest two shaking periods that are found in the table. The processor 121 may then display one or more massages on the display of the beverage container to warn the possibility of a spill.

Figure 15:
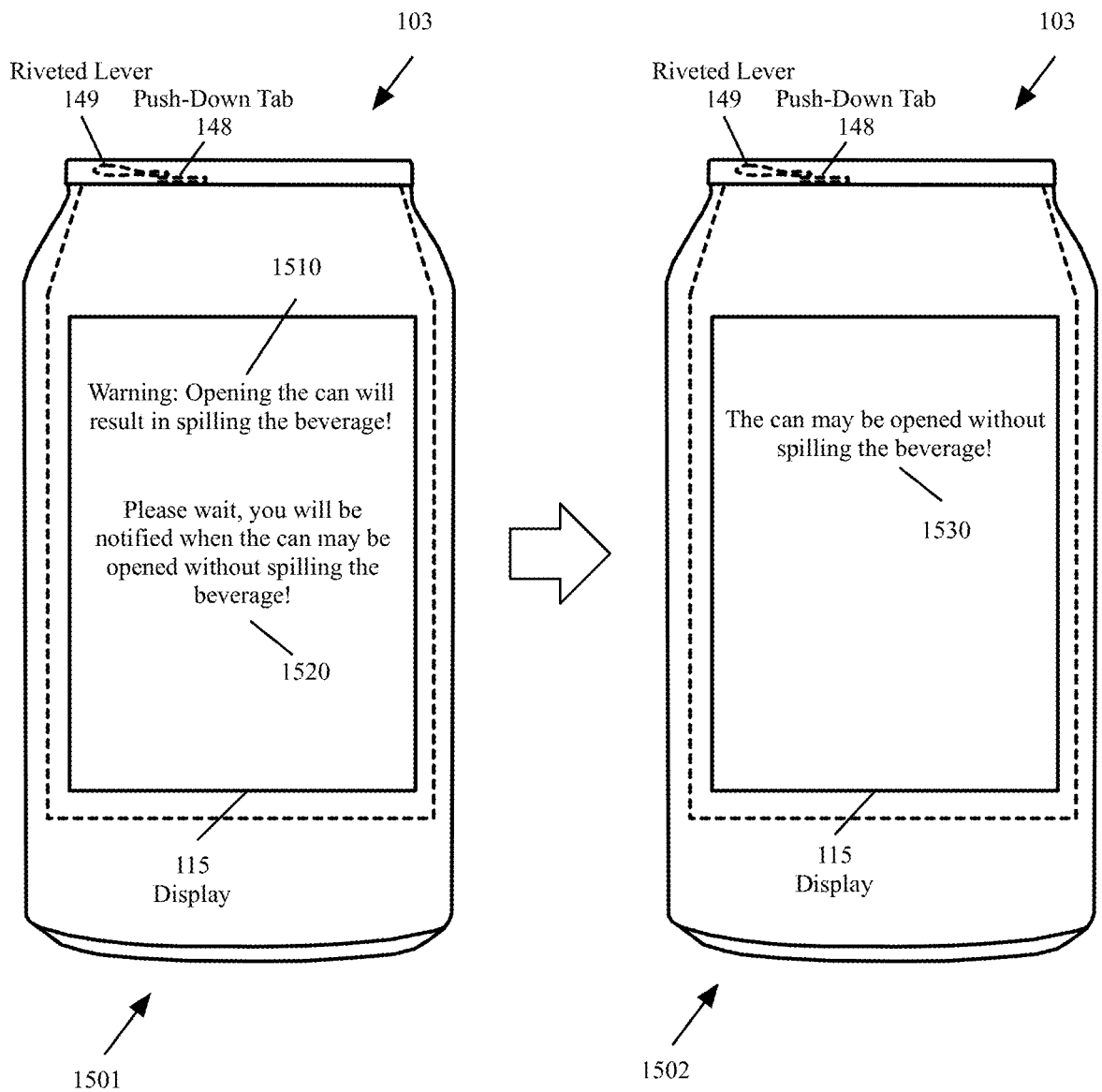
FIG. 15 illustrates a schematic front view of a beverage container illustrating messages being displayed on the electronic display of the beverage container to indicate whether or not opening the beverage container may result in a spill, according to various aspects of the present disclosure.

FIG. 15 illustrates a schematic front view of a beverage container illustrating messages being displayed on the electronic display of the beverage container to indicate whether or not opening the beverage container may result in a spill, according to various aspects of the present disclosure. Although a beverage can 103 is shown in the example of FIG. 15, the same discussion applies to the carbonated beverage bottle 102 of FIG. 1B. The example of FIG. 15 assumes that the beverage can 103 has been shaken for a period of time and the processor of the beverage can has used curves and/or table lookup as described above with reference to FIG. 14 to determine a rest period.

The figure, as shown, includes two stages 1501 and 1502. In stage 1501, the display 115 of the beverage container 103 is turned on (if not already on) by the processor 121 and a warning message 1510 may be displayed that opening the beverage container may result in a spill. Another message 1520 may indicate that a notification will be displayed when the beverage container may be opened without spilling.

In stage 1502, the rest period for the CO2 gas to be dissolved in the beverage may have reached. The processor 121 of the beverage container 103 may display a message 1530 on the display 115 indicating that the beverage container 103 may be opened without spilling the beverage.

Figure 16:
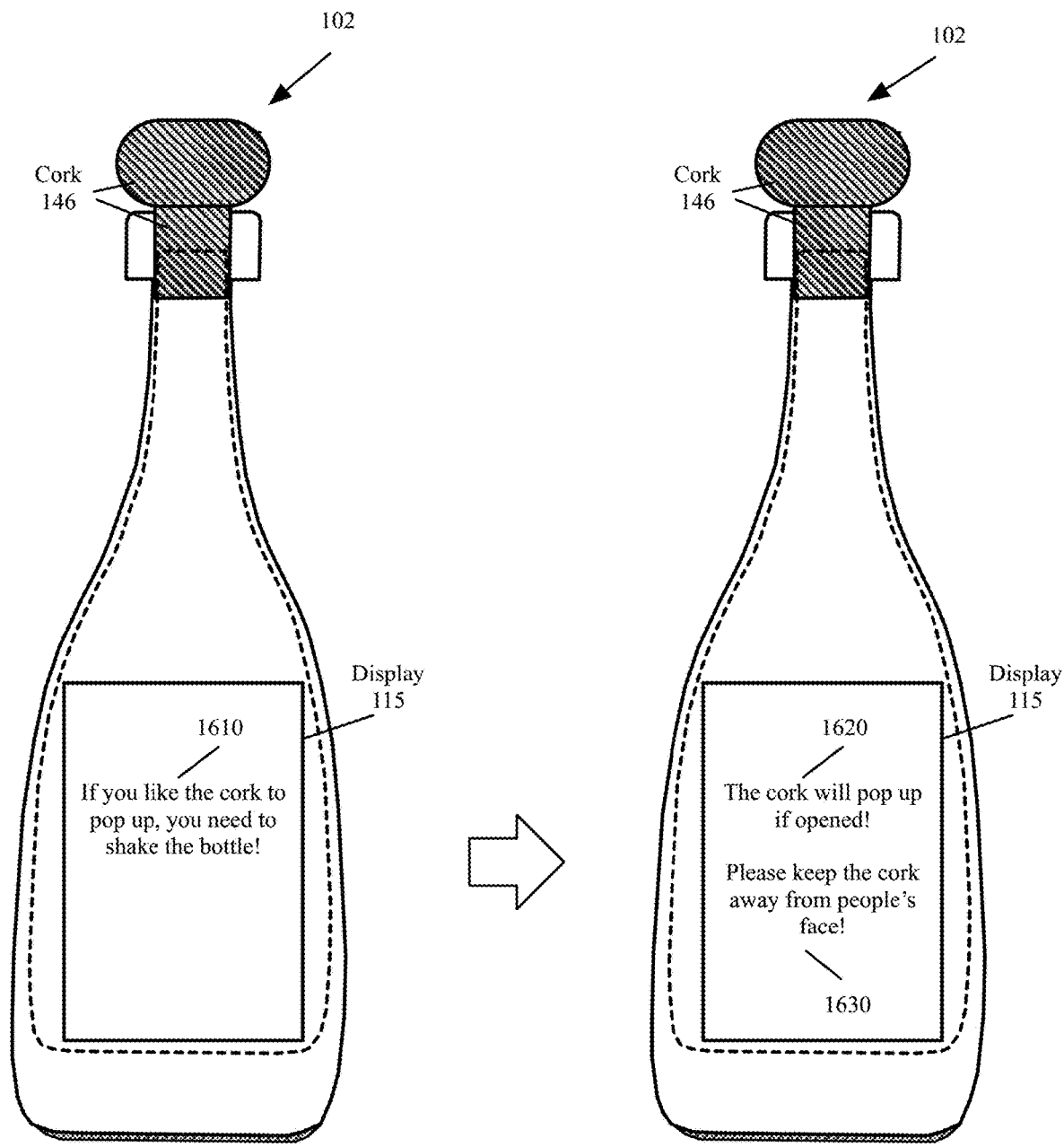
FIG. 16 is a schematic front view of a beverage container illustrating messages being displayed on the electronic display of the beverage container to indicate whether or not the cork of the beverage container may pop up when the cork is opened, according to various aspects of the present disclosure.

It should be noted that on some occasions, such as opening a champagne bottle, it may be desirable for the champagne bottle cork to pop up. The processor of a champagne bottle may be configured to indicate whether the cork may pop up after shaking. FIG. 16 is a schematic front view of a beverage container illustrating messages being displayed on the electronic display of the beverage container to indicate whether or not the cork of the beverage container may pop up when the cork is opened, according to various aspects of the present disclosure.

The example of FIG. 16 assumes that the champagne bottle 102 has not been shaken and the processor of the champagne bottle has used the curves and/or table lookup as described above with reference to FIG. 14 to determine that the cork may not pop up upon opening. The figure, as shown, includes two stages 1601 and 1602. In stage 1601, the processor of the beverage container 102 may have received one or more readings from the accelerometer of the beverage container indicting that the beverage container 102 is moving (e.g., the beverage container may have been picked up by a person). The processor 121 may turn on the display 115 of the beverage container 102 (if not already on) and a message 1610 may be displayed that if the user wishes for the cork 146 to pop up upon opening, the beverage container has to be shaken.

In stage 1602, the processor 121 of the beverage container 102 may have used the accelerometer reading and the curves and/or table lookup as described above with reference to FIG. 14 to determine that the cork may pop up upon opening. The processor may display a message 1620 on the display 115 to indicate that the cork will pop up if opened. The processor may also display a message 1630 to keep the cork away from people's face.

Figure 17:
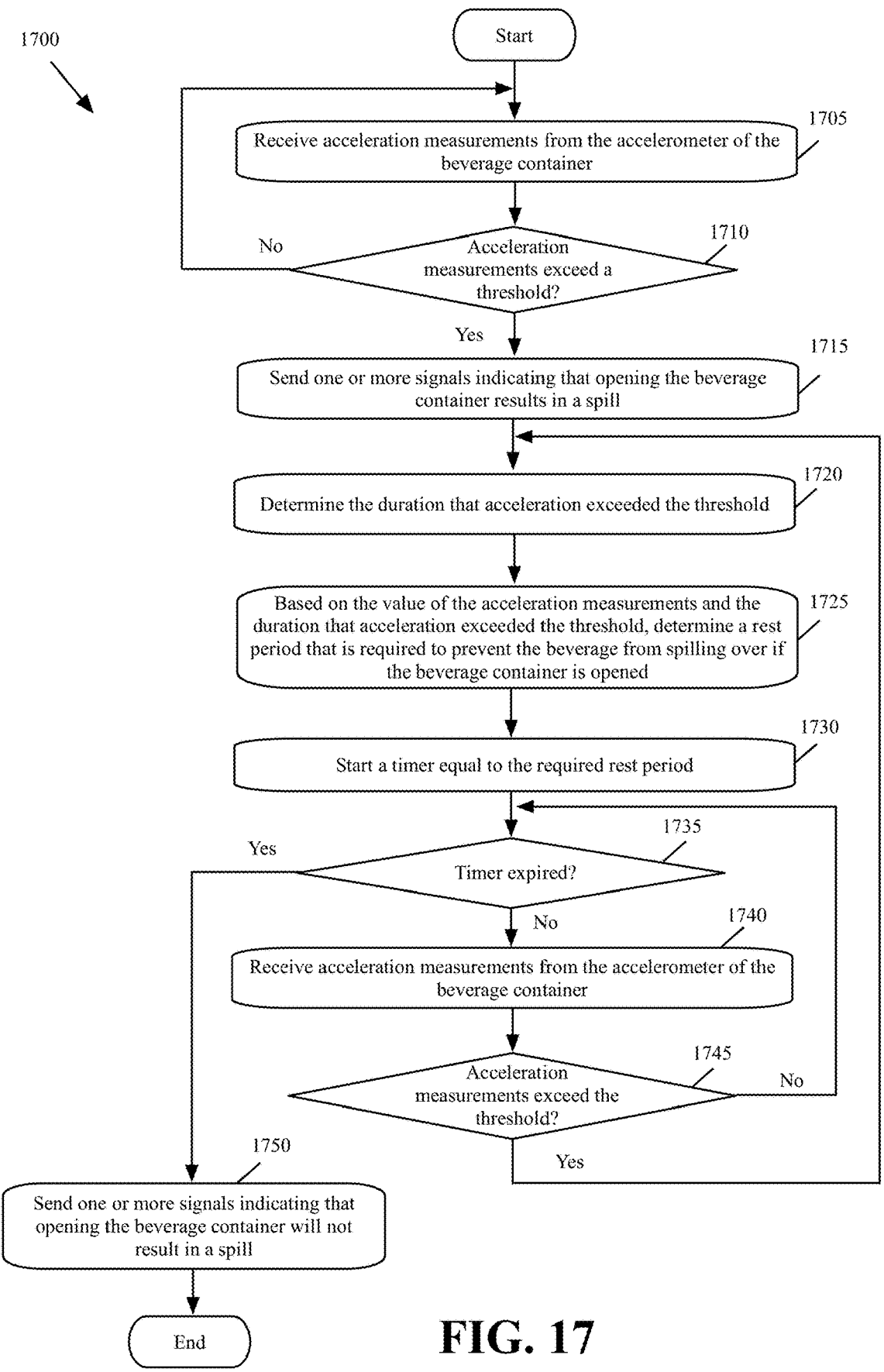
FIG. 17 is a flowchart illustrating an example process for determining whether the contents of a carbonated beverage container may spill based on acceleration measurements, according to various aspects of the present disclosure.

FIG. 17 is a flowchart illustrating an example process 1700 for determining whether the contents of a carbonated beverage container may spill based on acceleration measurements, according to various aspects of the present disclosure. The process 1700, in some embodiments, may be performed by the processor 121 (FIG. 1B or 1C) of a beverage container.

With reference to FIG. 17, the acceleration measurements from the accelerometer of the beverage container may be received (at block 1705). For example, the acceleration measurements may be received from the IMU 128 (or a separate accelerometer) at the processor 121 of the beverage container 103.

A determination may be made (at block 1710) whether the acceleration measurements exceed a threshold. The threshold may be the threshold beyond which, the contents of the beverage container may spill out if the beverage container is opened. As described above, the threshold may be determined by a set of experiments and may be stored in the memory of beverage container.

When the acceleration measurements do not exceed the threshold, the process 1700 may proceed back to block 1705, which was described above. Otherwise, one or more signals indicating that opening the beverage container results in a spill may be sent (at block 1715). For example, one or more signals may be sent by the processor 121 (FIG. 1B or 1C) to the display 115 to display one or messages, such as, the messages 1510 and 1520 of FIG. 15.

With further reference to FIG. 17, the duration that acceleration exceeded the threshold may be determined (at block 1720). For example, when several consecutive acceleration measurements exceed the threshold, the duration that acceleration exceeded the threshold is the time elapsed since the first consecutive acceleration measurement that exceeds the threshold.

Next, based on the value of the acceleration measurements and the duration that acceleration exceeded the threshold, a rest period may be determined (at block 1725) that is required to prevent the beverage from spilling over if the beverage container is opened. As described above with reference to FIGS. 13 and 14, for the type of beverage and the type of beverage container, the required rest period for the different acceleration values and durations may be determined by a set of experiments and may be stored in one or more tables in the memory of the beverage container. The rest period may then be determined by a table look up using the measured acceleration value and the acceleration duration.

A timer equal to the required rest period may be started (at block 1730). A determination may be made (at block 1735) whether the timer has expired. If yes, the process 1700 may proceed to block 1750, which is described below. Otherwise, the acceleration measurements from the accelerometer of the beverage container may be received (at block 1740). For example, the acceleration measurements may be received from the IMU 128 (or a separate accelerometer) at the processor 121 of the beverage container 103.

A determination may be made (at block 1745) whether the acceleration measurements exceed the threshold. If not, the process may proceed back to block 1735, which was described above. Otherwise, the process 1700 may proceed back to block 1720 to repeat blocks 1720-1730, including resetting the timer.

At block 1750, one or more signals may be sent indicating that opening the beverage container will not result in a spill. For example, one or more signals may be sent by the processor 121 (FIG. 1B or 1C) to the display 115 to display one or messages, such as, the message 1530 of FIG. 15. The process 1700 may then end.

Figure 18:
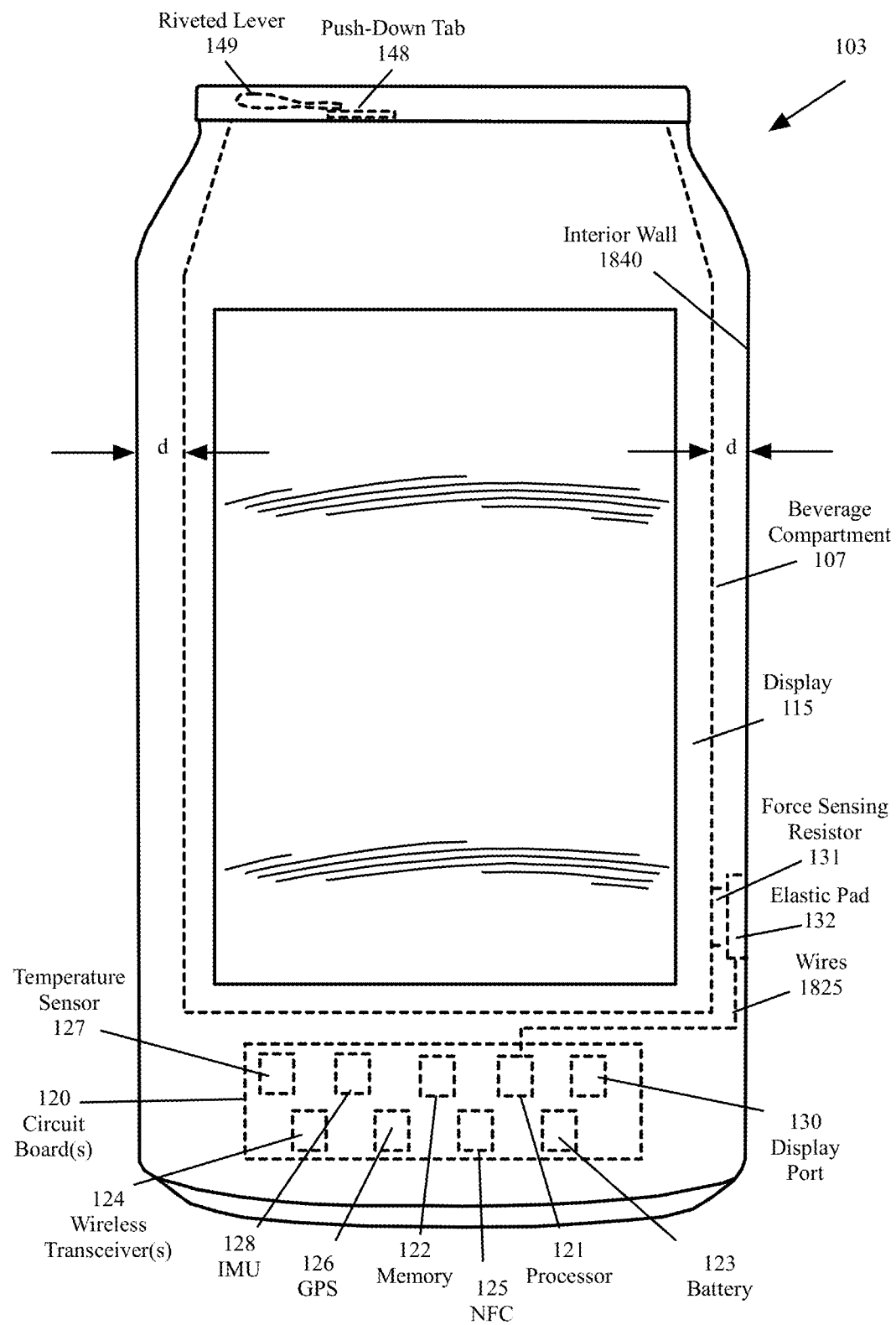
FIG. 18 is a functional diagram illustrating an example carbonated beverage container that may include a force sensing resistor for to determine whether opening a beverage container may result in spilling the contents, according to various aspects of the present disclosure, according to various aspects of the present disclosure.

In addition to, or in lieu of, using the methods described above with reference to FIGS. 13 and 14, the beverage container, in some embodiments may include a force sensing resistor, a pressure sensor and/or a distance sensor to determine the amount of pressure in a carbonated beverage container, such as a soda can or a beer can. FIG. 18 is a functional diagram illustrating an example carbonated beverage container that may include a force sensing resistor to determine whether opening a beverage container may result in spilling the contents, according to various aspects of the present disclosure.

With reference to FIG. 18, the beverage container 103 may be an aluminum can. The beverage compartment 107, in some embodiments, may be made of a flexible material. For example, the beverage compartment 107, may be made of a thin layer of metal, such as aluminum. Although the following discussions refer to a can 103 of carbonated beverage, the same discussion applies to a bottle of carbonated beverage, such as the bottle 102 of FIG. 1B, when the compartment 106 is made of a flexible material, such as plastic.

When the beverage container 103 is shaken, the $CO_2$ gas that is dissolved in the liquid may be released in the air above the liquid inside the beverage compartment 107, causing the pressure inside the beverage compartment 107 to increase. As the pressure inside the beverage compartment 107 increases, the flexible beverage compartment 107 may expand, resulting in the distance, d, between the beverage compartment 107 and the interior wall 1840 of the beverage container 103 to decrease.

With reference to FIG. 18, the beverage container 103 may a force sensing resistor 131, which may be connected to the processor 121 wirelessly or by a set of wires 1825. The beverage container 103, in some embodiments, may include a pad 132. The pad 132, in some embodiments, may be elastic. For example, and without limitations, the pad 132 may be made of rubber, or a synthetics rubber material, such as, neoprene, etc.

The force sensing resistor 131, in some embodiments, may be a thin, commercially available sensor, which may exhibit dynamic resistance related to the amount of force applied to the surface of the sensor. The more force is applied to the surface of the sensor, the lower the resistance would be. The resistance change may, therefore, be inversely proportional to the applied force.

As shown in FIG. 18, the pad 132 and the force sensing resistor 131 may be fitted in the gap between the beverage compartment 107 and the interior wall 1840 of the beverage container 107. The force sensing resistor 131 may typically have a thickness of 0.3 to 0.8 millimeter (mm). The thickness of the elastic pad 132 may be configured such that when an equilibrium is made between the CO2 that is dissolved in the liquid and the CO2 that is trapped in the air above the liquid inside the beverage compartment 107, the force sensing resistor 131 may be in touch with the beverage compartment 107 and the elastic pad 132 may snuggly fit between the force sensing resistor 131 and the interior wall 1840.

The processor 121 of the beverage container 103 may receive and store the parameters measured by the force sensing resistor 131. The processor 121 may receive the parameters measured by the force sensing resistor 131 when there is an equilibrium between the CO2 that is dissolved in the liquid and the CO2 that is trapped in the air above the liquid inside the beverage compartment 107. For example, during a setup (or initialization) procedure, the beverage container 103 may be kept at rest for a rest period (e.g., as described above with reference to FIGS. 13 and 14) that is required for the equilibrium to be established. The processor 121 may store the force measurement at the equilibrium-state force measurement.

During operation, the processor 121 may receive the force measurements from the force sensing resistor 131. As the beverage container 103 is shaken, the CO2 gas in the beverage is released in the air above the liquid inside the beverage compartment 107, the pressure inside the beverage compartment 107 increases and the flexible beverage compartment 107 expands. As the flexible beverage compartment 107 expands, the beverage compartment 107 exerts more force on the surface of the force sensing resistor 131. The elastic pad 132 that is fit between the force sensing resistor 131 and the interior wall 1840 of the beverage container 103 allows the force sensing resistor 131 to continue measuring the force (e.g., without reaching a maximum and being saturated).

The processor may determine whether the difference between the current force measured by the force sensing resistor 131 and the stored equilibrium-state force measurement exceeds a predetermined threshold. The threshold, in some embodiments, may be determined by a set of experiments and may have been stored in the memory 122 of the beverage container 103. In each experiment, a can or a bottle of carbonated beverage may be shaken and the force measurements made by the force sensing resistor 131 may be stored in one or more tables. The can or the bottle is then opened. A determination may be made whether or not the beverage spills out.

The determination, in some embodiments, may be made by a sensor placed outside the opening of the beverage container to detect any spilled liquid. The determination, in some embodiments, may be visually made by a person. For the same type of container, the same type of beverage, a can or bottle may be opened after different values of force are measured by the force sensing resistor 131. The value of the measured force above which the contents of the can or bottle are spilled out upon the opening may be used as the threshold force value for the particular type of container and the particular type of beverage. The values of the threshold force may be stored in the memory 122 of the beverage container 103. Some embodiments may use a first force threshold to determine that the beverage may spill out and a second threshold (which may be smaller than the first threshold) to safely determine that the beverage may not spill out upon opening.

In addition to, or in lieu of, the force sensing sensor 131, the beverage container 103 may include one or more pressure sensor(s) or one or more distance sensor(s). The pressure senso may include a spring that may be snugly placed between the beverage compartment 107 and the interior wall 1740 of the beverage container 103. As the pressure of the gas in the beverage compartment 107 increases or decreases, the spring may compress or stretch. The pressure inside the beverage compartment 107 may be determined as a function of the compressing or stretching of the spring or by using the results of a set of experimentations similar to the experimentations described with reference to FIGS. 13, 14, and 18.

The distance sensor may measure the capacitance between the beverage compartment 107 and the interior wall 1840 of the beverage container 103. The change in the distance between the beverage compartment 107 and the interior wall 1840 of the beverage container 103 may be determined as a change in the capacitance between the beverage compartment 107 and the interior wall 1840 of the beverage container 103. The pressure inside the beverage compartment 107 may be calculated based on the distance, d (e.g., by using the results of a set of experimentations similar to the experimentations described with reference to FIGS. 13, 14, and 18).

Figure 19:
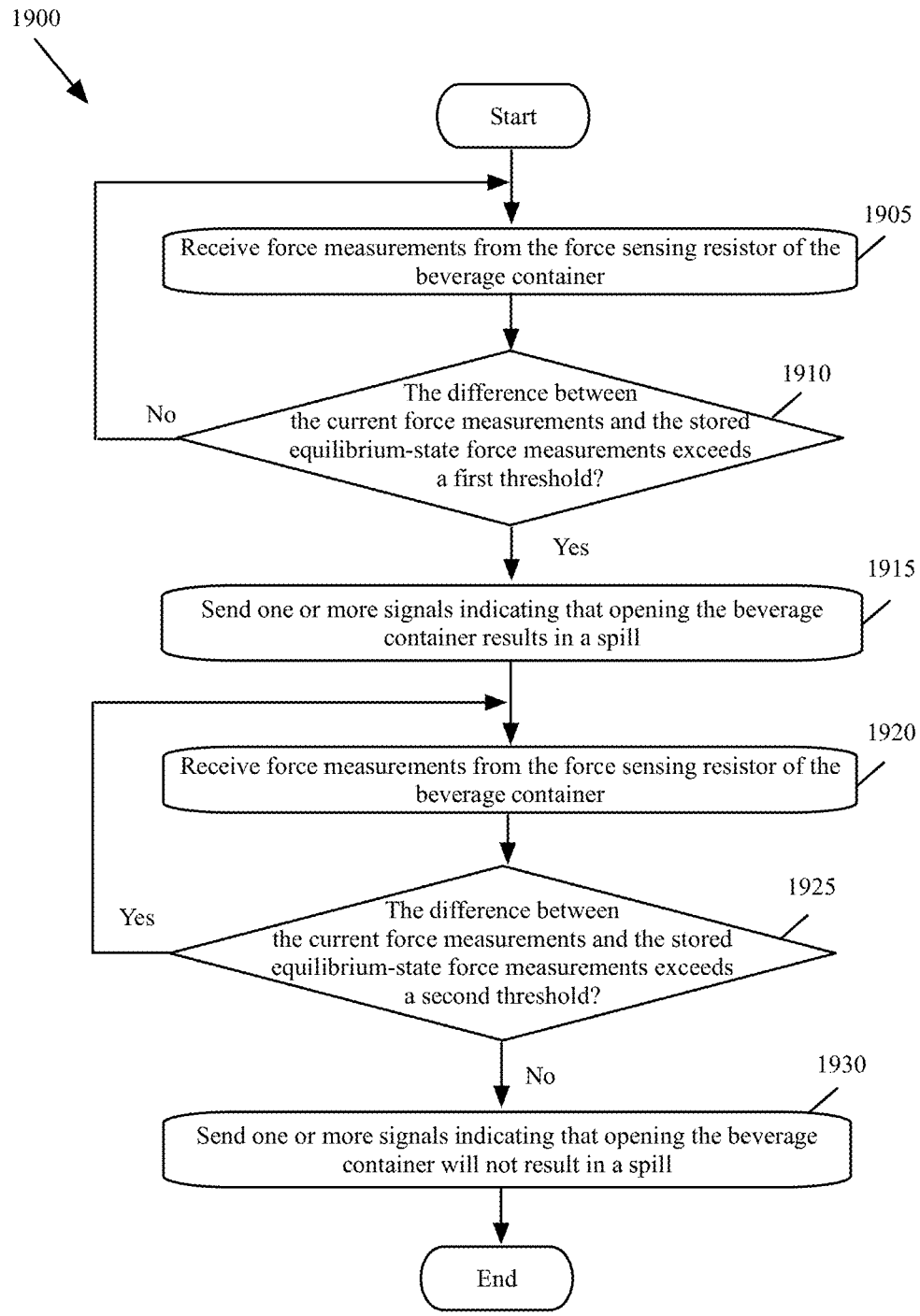
FIG. 19 is a flowchart illustrating an example process for determining whether the contents of a carbonated beverage container may spill based on force measurements, according to various aspects of the present disclosure.

FIG. 19 is a flowchart illustrating an example process 1900 for determining whether the contents of a carbonated beverage container may spill based on force measurements, according to various aspects of the present disclosure. The process 1900, in some embodiments, may be performed by the processor 121 (FIG. 1B or 1C) of a beverage container.

With reference to FIG. 19, the force measurements from the force sensing resistor of the beverage container may be received (at block 1905). For example, the force measurements may be received from the force sensing resistor 131 of FIG. 18 at the processor 121 of the beverage container 102 or 103. A determination may be made (at block 1910) whether the difference between the current force measurements and the stored equilibrium-state force measurements exceeds a first threshold. If not, the process 1900 may proceed back to block 1905, which was described above.

Otherwise, one or more signals may be sent (at block 1915) indicating that opening the beverage container results in a spill. For example, one or more signals may be sent by the processor 121 (FIG. 1B or 1C) to the display 115 to display one or messages, such as, the messages 1510 and 1520 of FIG. 15. Next, the force measurements from the force sensing resistor of the beverage container may be received (at block 1920). For example, the force measurements may be received from the force sensing resistor 131 of FIG. 18 at the processor 121 of the beverage container 103. A determination may be made (at block 1925) whether the difference between the current force measurements and the stored equilibrium-state force measurements exceeds a second threshold. If not, the process 1900 may proceed back to block 1920, which was described above.

Otherwise, one or more signals may be sent (at block 1930) indicating that opening the beverage container will not result in a spill. For example, one or more signals may be sent by the processor 121 (FIG. 1B or 1C) to the display 115 to display one or messages, such as, the message 1530 of FIG. 15. The process 1900 may then end.

V. Display Control

The processor of the beverage container in some embodiments, may provide different controls on the display of the beverage container. The display may be turned off after a period of inactivity. The processor may adjust the orientation of the display when the beverage container is tilted. The display may be turned off during transportation.

A. Turning the Display on and Off Based on Different Criteria

The processor 121 of the beverage containers 101-103 (FIGS. 1A-1C) may turn off the display 115 based on one or more criteria. For example, the processor 121 may turn off the display if the beverage bottle has not moved for a predetermined time period. The predetermined time period, in some embodiments, may be adjustable through the UI of an authorized electronic device and/or through an option displayed on the display 115 of the beverage container. As described above with reference to stage 401 of FIG. 4, the display may be turned on when a touch gesture is received on the display 115 of the beverage container.

The beverage container, in some embodiments, may include a touch sensor (not shown) that may be used to turn the display on or off. The processor 121, in some embodiments, may turn on the display when a movement of the beverage container is detected (e.g., by the accelerometer of the beverage container). As described above with reference to FIG. 8, the processor 121 may turn on the display to display a message when one or more criteria are met.

B. Adjusting the Display Orientation

Figure 20:
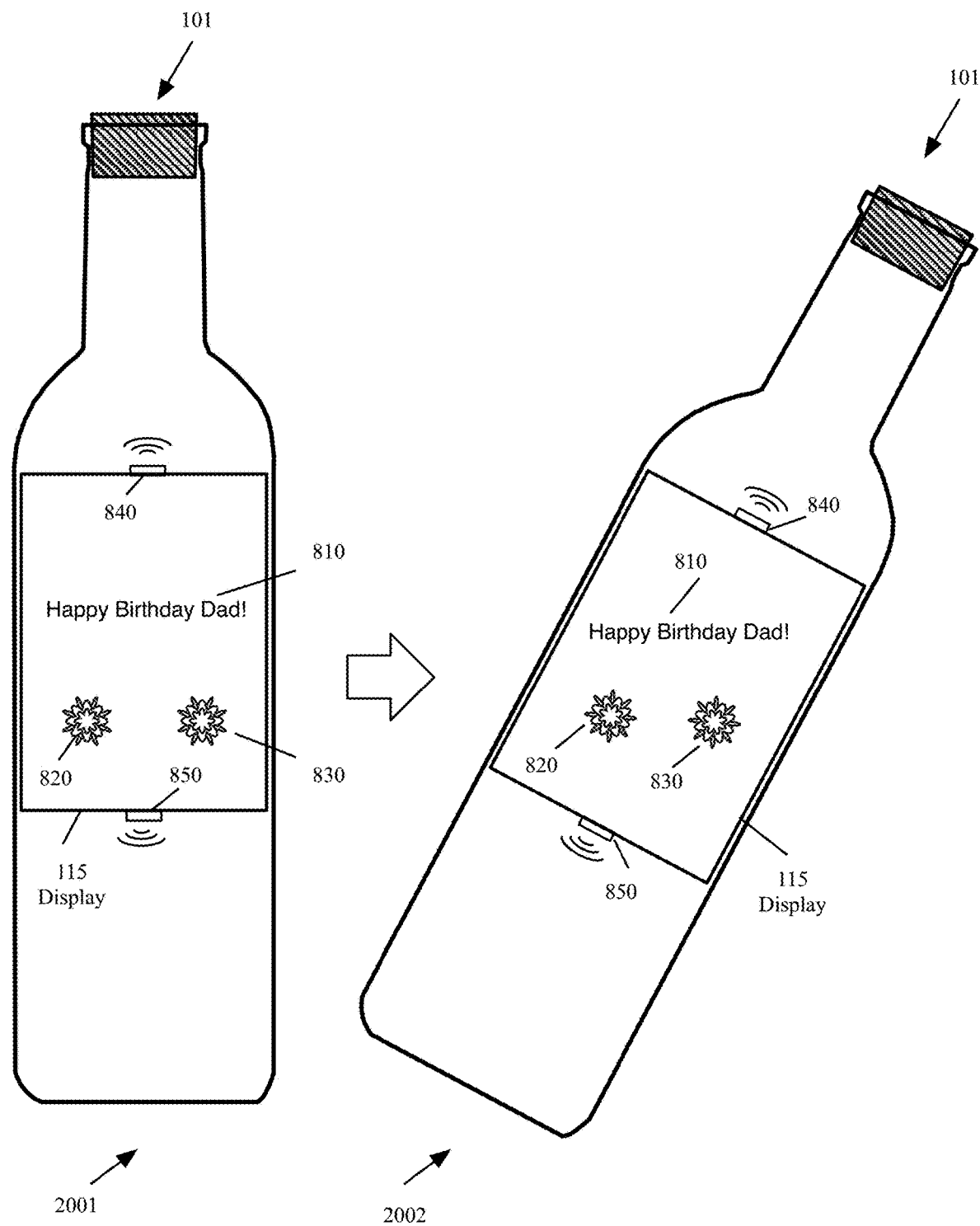
FIG. 20 illustrates a schematic front view of a beverage container that may adjust the orientation of the displayed content when the beverage container is tilted, according to various aspects of the present disclosure.

Some embodiments may determine that a beverage container is tilted and may adjust the orientation of the displayed content on the beverage container's electronic display accordingly. FIG. 20 illustrates a schematic front view of a beverage container that may adjust the orientation of the displayed content when the beverage container is tilted, according to various aspects of the present disclosure.

The figure, as shown, includes two stages 2001 and 2002. In stage 2001, the beverage container is in a substantially vertical orientation. As shown, the message 810 and the animations 820-830 are displayed substantially similar to stage 802 of FIG. 8.

In stage 2002, the beverage container 101 may be tilted. The magnetometer and/or the gyroscope of the beverage container may be used by the processor 121 to determine that the beverage container is tilted. As shown, the processor 121 may use the angle that the beverage container is tilted to adjust the orientation of the message 810 and the location of the animations 820-830 on the display 115 of the beverage container 101. Although a wine bottle 101 is shown in the example of FIG. 20, the discussions regarding adjusting the display orientation applies to any of the beverage containers 101-103 of FIGS. 1A-1C, respectively

C. Transport Mode

In some embodiments, the display of the beverage container may be turned off during transportation. The beverage container may be placed in a transport mode by an option (not shown) provided by the beverage container application 220 (FIG. 2) or an option 614 (FIG. 6) displayed on the display of the beverage container. In some embodiments, when the beverage container is in transport mode, the display may not turn on, for example to conserve battery power.

The beverage container may subsequently be taken out of the transport mode. For example, the processor of the beverage container may receive one or more signals from an authorized external electronic device to terminate the transport mode. Alternatively, the processor of the beverage container may take the beverage container out of transport mode when a specific touch gesture is received on the touchscreen of the electronic display.

Figure 21:
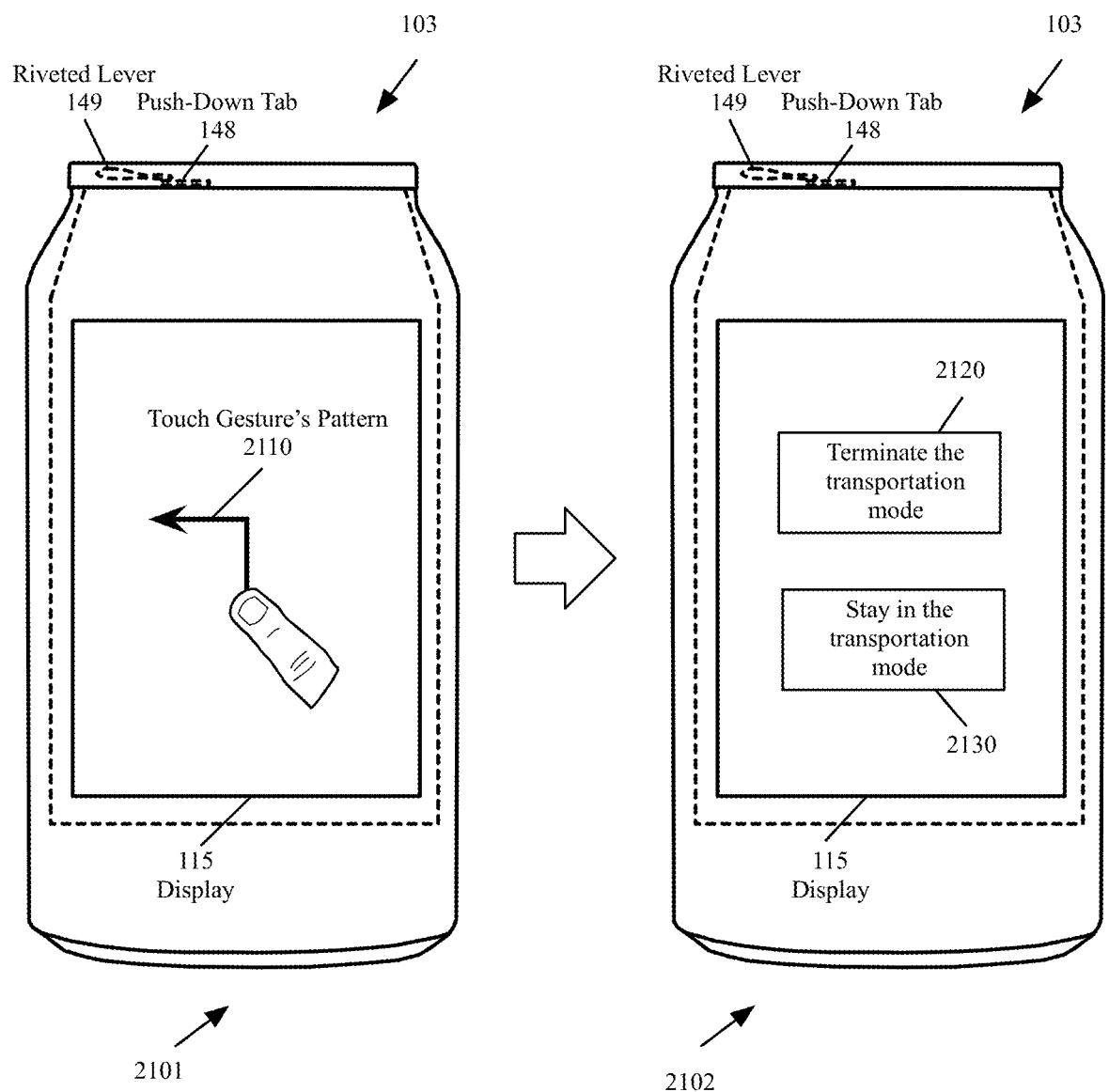
FIG. 21 illustrates a schematic front view of a beverage container that may be taken out of transport mode after receiving a touch gesture on the touchscreen of the beverage container, according to various aspects of the present disclosure.

FIG. 21 illustrates a schematic front view of a beverage container that may be taken out of transport mode after receiving a touch gesture on the touchscreen of the beverage container, according to various aspects of the present disclosure. Although a beverage can 103 is shown in the example of FIG. 21, the discussions regarding the transport mode applies to any of the beverage containers 101-103 of FIGS. 1A-1C, respectively. In the example of FIG. 21, it is assumed that the beverage container 103 has been placed in transport mode to keep the display 115 of the beverage container off. It is also assumed that the display 115 is a touchscreen.

The figure, as shown, includes two stages 2101 and 2102. In stage 2101, a touch gesture with a predetermined pattern 2110 may be applied on the touchscreen 115. The beverage container, in some embodiments, may come out of the transport mode once the touch gesture with the specific pattern is received. In other embodiments, such as the embodiment depicted in FIG. 21, the display 115 may display the options 2101 and 2102. As shown in stage 2102, the option 2120 may be selected to confirm that the transport mode is to be terminated. The option 2130 may be selected to keep the beverage container in the transport mode, resulting in the display to be turned off again.

VI. Storage Control

Some embodiments may provide storage control for specific types of beverage containers, such as wine bottles, champagne bottles, carbonated beverage bottles or cans, etc. Wine bottles are preferably stored in a horizontal orientation to keep the bottle's cork wet to prevent the outside air to enter the beverage compartment. Different types of wine bottles may also be kept in a specific range of temperature to prevent the wine to oxidize and/or to turn into vinegar. Other types of beverages may lose flavor and/or carbonation after a prolonged storage period, after being exposed to extreme temperatures, etc.

Figure 22:
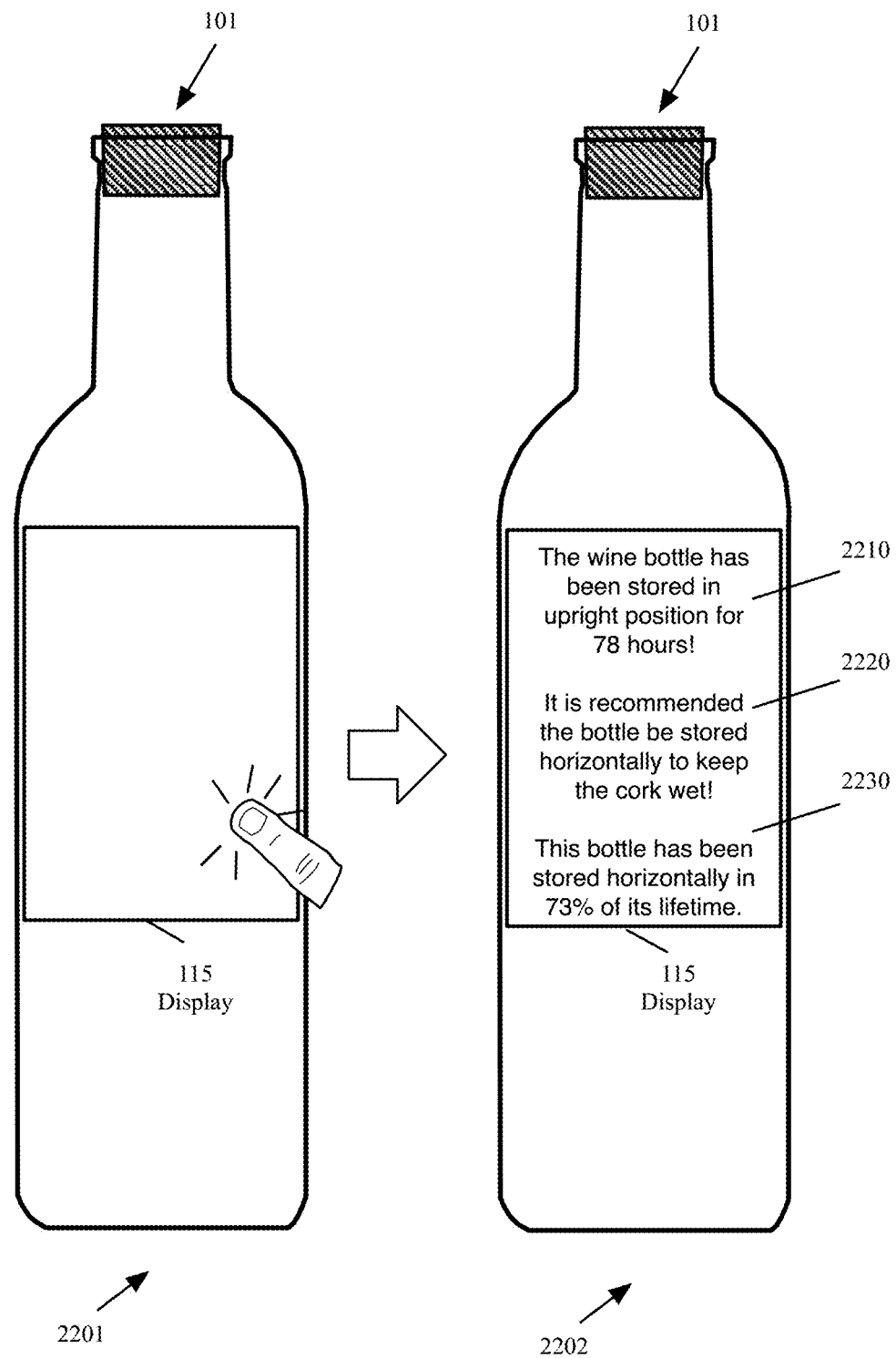
FIG. 22 illustrates a schematic front view of a beverage container that may provide assistance regarding the storage orientation and/or may display storage orientation statistics, according to various aspects of the present disclosure.

FIG. 22 illustrates a schematic front view of a beverage container that may provide assistance regarding the storage orientation and/or may display storage orientation statistics, according to various aspects of the present disclosure. The figure, as shown, includes two stages 2201 and 2202. In stage 2201, the display 115 of the beverage container may be turned on, for example, after receiving a touch gesture, after the beverage container is moved, and/or after a touch sensor (not shown) is touched on the beverage container.

As shown in stage 2202, the processor of the beverage container 101 may display one or more messages 2210-2230 to provide assistance for the storage of the beverage container. In the example of FIG. 22, the processor of the beverage container may have used the parameters received from the gyroscope and/or from the magnetometer of the beverage container to determine that the wine bottle has been kept in upright position longer than a threshold time period.

The processor may display the message 2210 to indicate the time period that the wine bottle has been stored in upright position. The processor may display the message 2220 to indicate a recommendation for storing the wine bottle. The processor, in some embodiments, may store statistics regarding the storage orientation of the beverage container 101. The processor may display the message 2230 to indicate the history of the wine bottle's storage.

Figure 23:
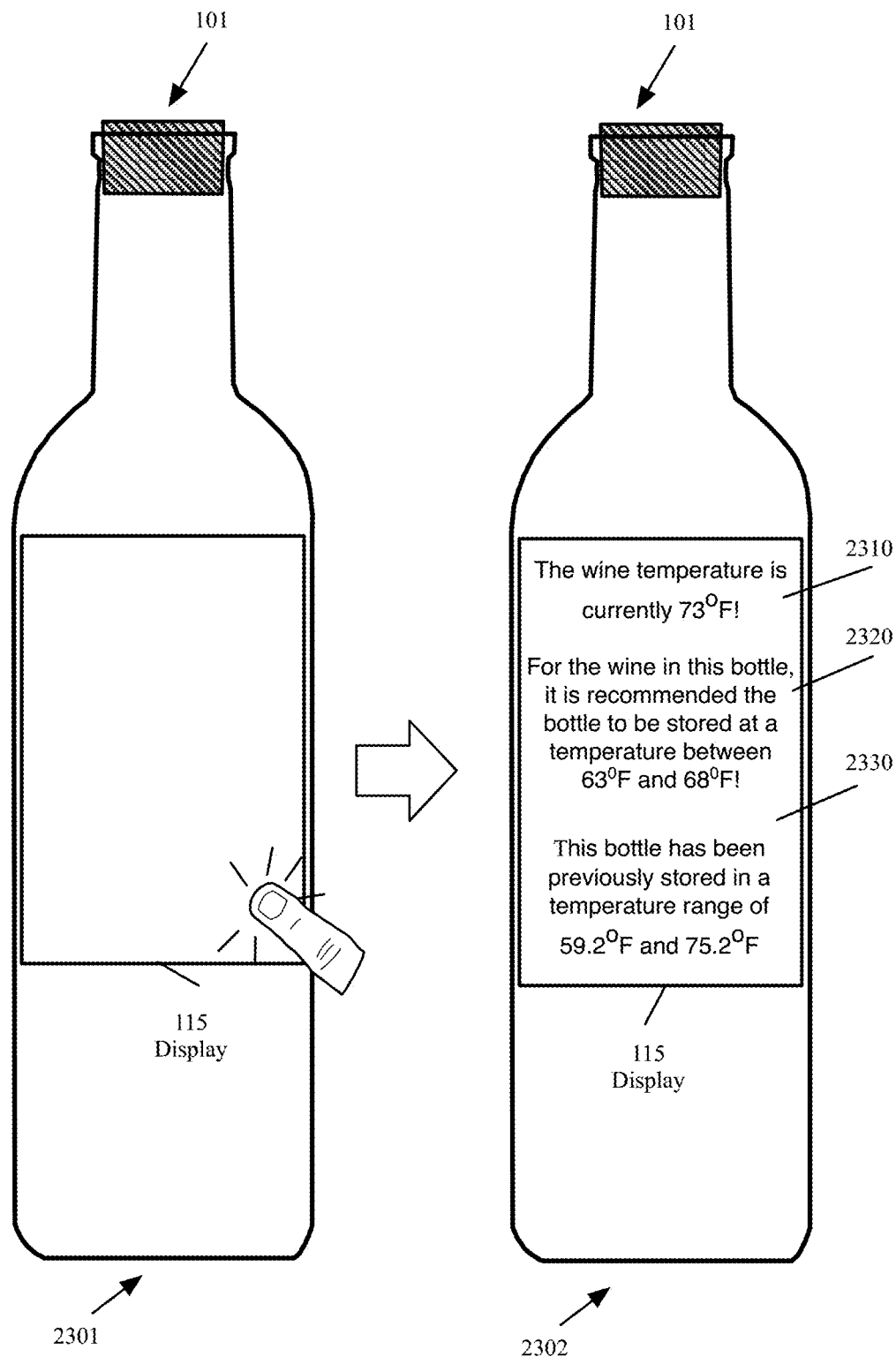
FIG. 23 illustrates a schematic front view of a beverage container that may provide assistance regarding the storage temperature and/or may display storage temperature statistics, according to various aspects of the present disclosure.

FIG. 23 illustrates a schematic front view of a beverage container that may provide assistance regarding the storage temperature and/or may display storage temperature statistics, according to various aspects of the present disclosure. The figure, as shown, includes two stages 2301 and 2302. In stage 2301, the display 115 of the beverage container may be turned on, for example after receiving a touch gesture, after the beverage container is moved, and/or a touch sensor (not shown) is touched on the beverage container.

As shown in stage 2302, the processor of the beverage container 101 may display one or more messages 2310-2330 to provide assistance for the storage temperature of the beverage container. In the example of FIG. 23, the processor of the beverage container may have used the parameters received from the temperature sensor 127 of the beverage container to determine the current temperature inside the wine bottle.

The processor may display the message 2310 to indicate the current temperature of the wine bottle. The processor may display the message 2320 to indicate a recommended range of temperature for storing the particular type of wine in the wine bottle 101. The processor, in some embodiments, may store statistics regarding the temperature of the beverage container 101. The processor may display the message 2330 to indicate the history of the wine bottle's temperature.

With reference to FIG. 23, similar messages may be displayed for the beverage containers 102-103 of FIGS. 1B-1C, respectively. For example, similar messages may display information regarding the storage temperature and/or may display storage temperature statistics regarding the containers 102-103.

In some embodiments, the processor 121 of the beverage container 101-103 may receive temperature measurements from the temperature sensor 127 and may control the color of the display 115 based on the temperature measurements. For example, for a beer or soda beverage where it is desirable for the beverage to be consumed cold (e.g., the temperature to be below a first threshold), the processor 121 may compare the temperature measurements with the first threshold and may change the color of the display 115 to a first color (e.g., and without limitations by changing all, or a majority of, the display pixels to blue) when the temperature measurements are below the first threshold.

To alert the user that the beverage temperature may be higher than desirable, the processor 121 may compare the temperature measurements with a second threshold (which may be a larger value than the first threshold) and may change the color of the display 115 to a second color (e.g., and without limitations by changing all, or a majority of, the display pixels to red) when the temperature measurements are above the second threshold.

VII. Changing the Language

The processor of the beverage container, in some embodiments, may change the language used to display messages on the display of the beverage container and/or the language used to play messages on the speakers of the beverage container. The language change may be done when the processor of the beverage container receives one or more signals from an authorized external electronic device and/or from an option on the display of the beverage container. The processor of the beverage container, in some embodiments, may be configured to automatically change the language when one or more criteria are met.

Figure 24:
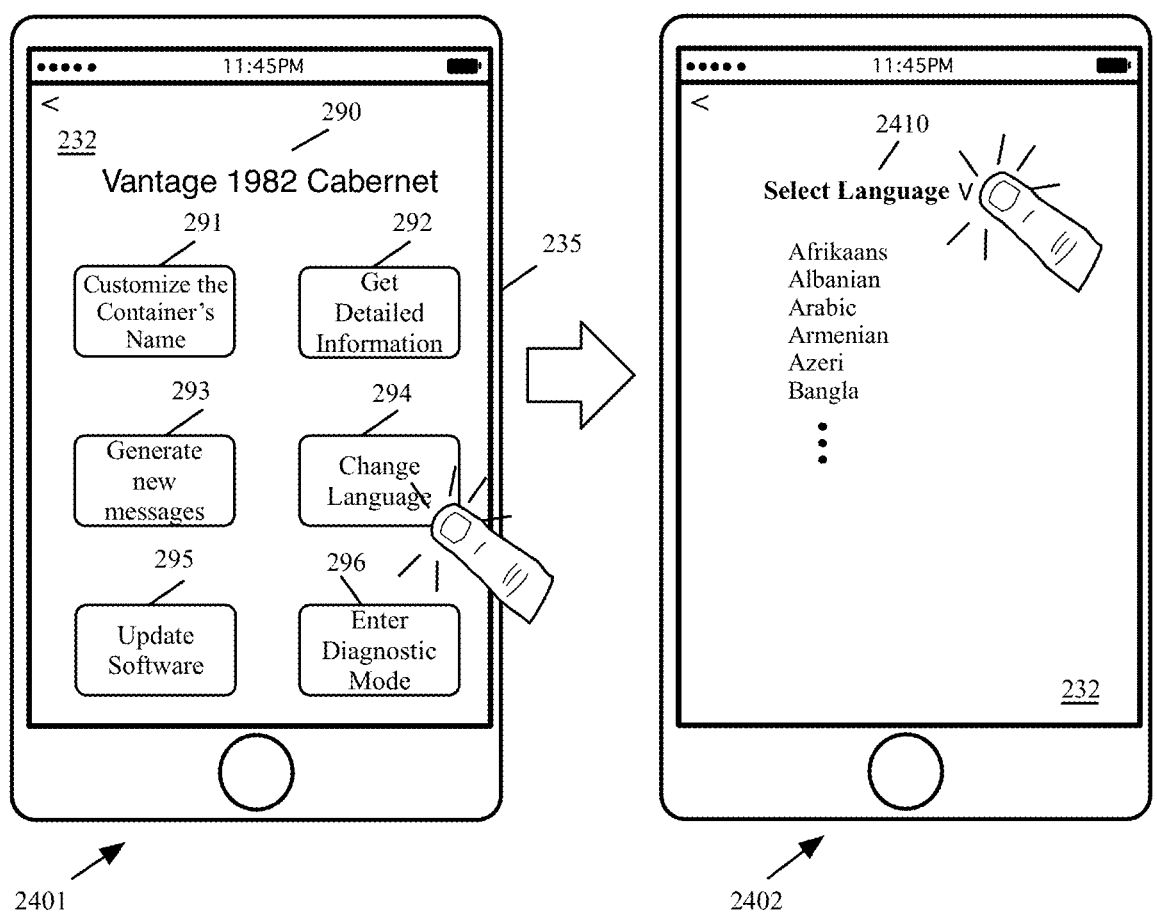
FIG. 24 illustrates a schematic front view of an electronic device that may include an application program for changing the language of the messages displayed by the beverage container, according to various aspects of the present disclosure.

FIG. 24 illustrates a schematic front view of an electronic device that may include an application program for changing the language of the messages displayed by the beverage container, according to various aspects of the present disclosure. The electronic device 235 of FIG. 24 may be communicatively coupled with any of the beverage containers 101-103 through a wired connection (e.g., through the USB port 1110 and cable 1130 of FIGS. 11A-11B) or a wireless connection (e.g., through the e.g., through the Bluetooth transceiver, the Wi-Fi transceiver, the IR transceiver, and/or the NFC chip described above).

The figure, as shown, includes two stages 2401 and 2402. Stage 2401 may display similar options 291-296 as stage 204 of FIG. 2. As shown in stage 2401, the option 294 may be selected to change the language for displaying the messages on the beverage container. In response, the UI 232, in stage 2402, display a list (e.g., a drop down menu) 2410 of the languages that the user may select for the messages. The language may also be changed by selecting an option similar to the option 294 that may be displayed on the display of the beverage container.

The language, in some embodiments, may be automatically changed based on one or more criteria. For example, the processor of the beverage container may receive location information from the GPS receiver 126 (FIG. 1A-1C) of the beverage container and/or from one or more electronic devices. The processor may determine that the beverage container has entered a region that uses a different language. When messages are available in the memory 122 of the beverage container in the language used in the new region, the processor may automatically change the language for displaying messages and/or for playing messages on the speakers of the beverage container.

Figure 25:
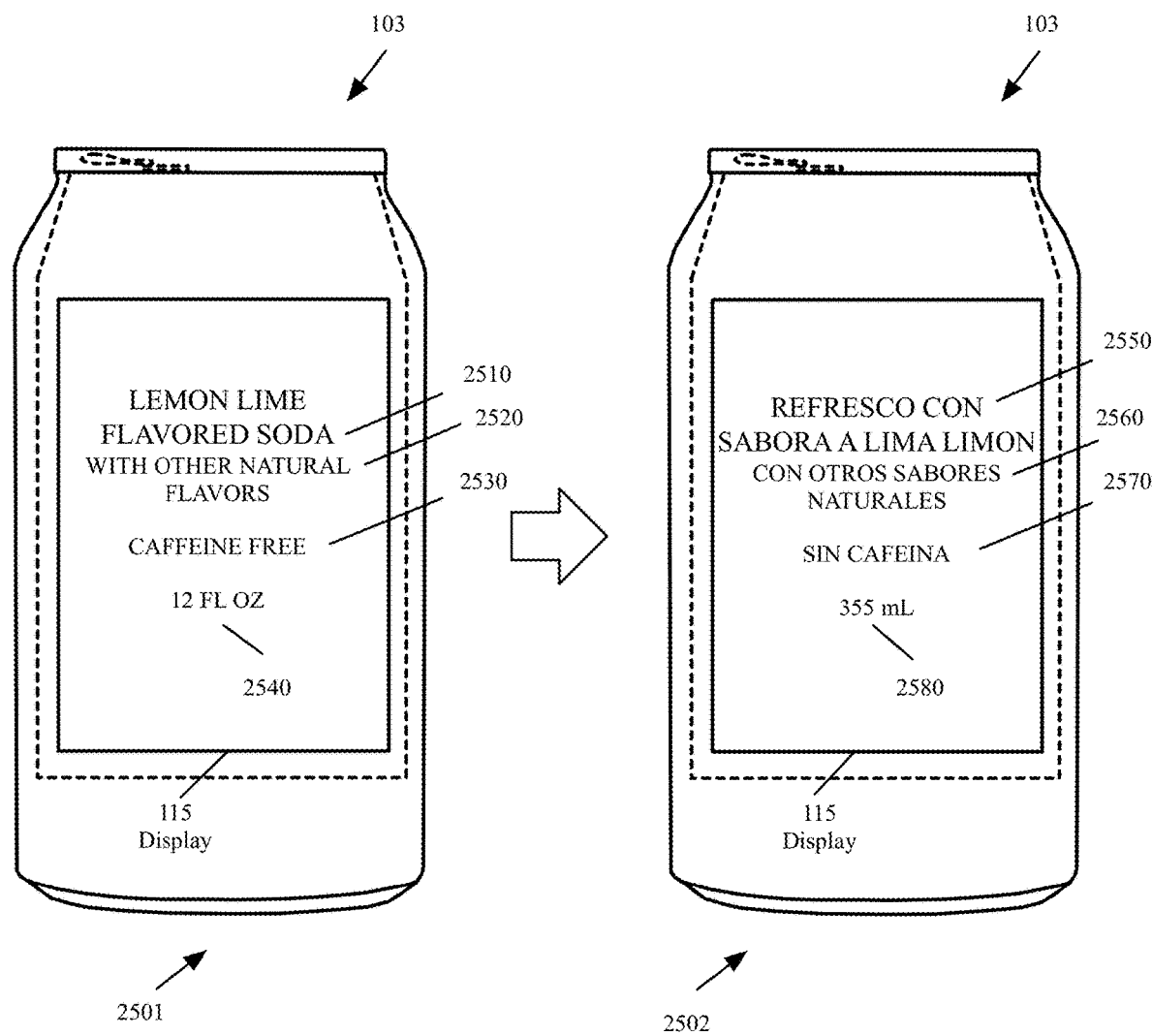
FIG. 25 illustrates a schematic front view of a beverage container that may change the language based on one or more criteria, according to various aspects of the present disclosure.

FIG. 25 illustrates a schematic front view of a beverage container that may change the language based on one or more criteria, according to various aspects of the present disclosure. Although a beverage can 103 is shown in the example of FIG. 25, the discussions regarding the changing of the language applies to any of the beverage containers 101-103 of FIGS. 1A-1C, respectively. The figure, as shown, includes two stages 2501 and 2502. In stage 2501, several messages 2510-2540 are displayed on the display 115 of the beverage container 103.

In this example, it is assumed that the beverage container, in stage 2502 has entered a region that uses a different language than the region where the beverage container was in stage 2501. For example, the processor of the beverage container 103 may have received location information from the GPS receiver 126 (FIG. 1A-1C) of the beverage container and/or from one or more electronic devices and may have determined that the language in the new region is different than the language in the previous region.

When message in the language of the new region are available in the memory storage of the beverage container and the processor of the beverage container is configured to automatically change the language, the processor may display the messages in the language of the new region. As shown in stage 2502, the messages 2550-2580 may be translations of the messages 2510-2540. As shown by the messages 2540 and 2580, the processor, in some embodiments, may also change the units of measure to units of measure used in the new region. In the embodiments that the beverage container has one or more speakers, the messages played from the speakers may also be translated, when appropriate (e.g., when the played words describe a feature of the beverage rather than being a song).

VIII. Diagnostic Mode

Figure 26:
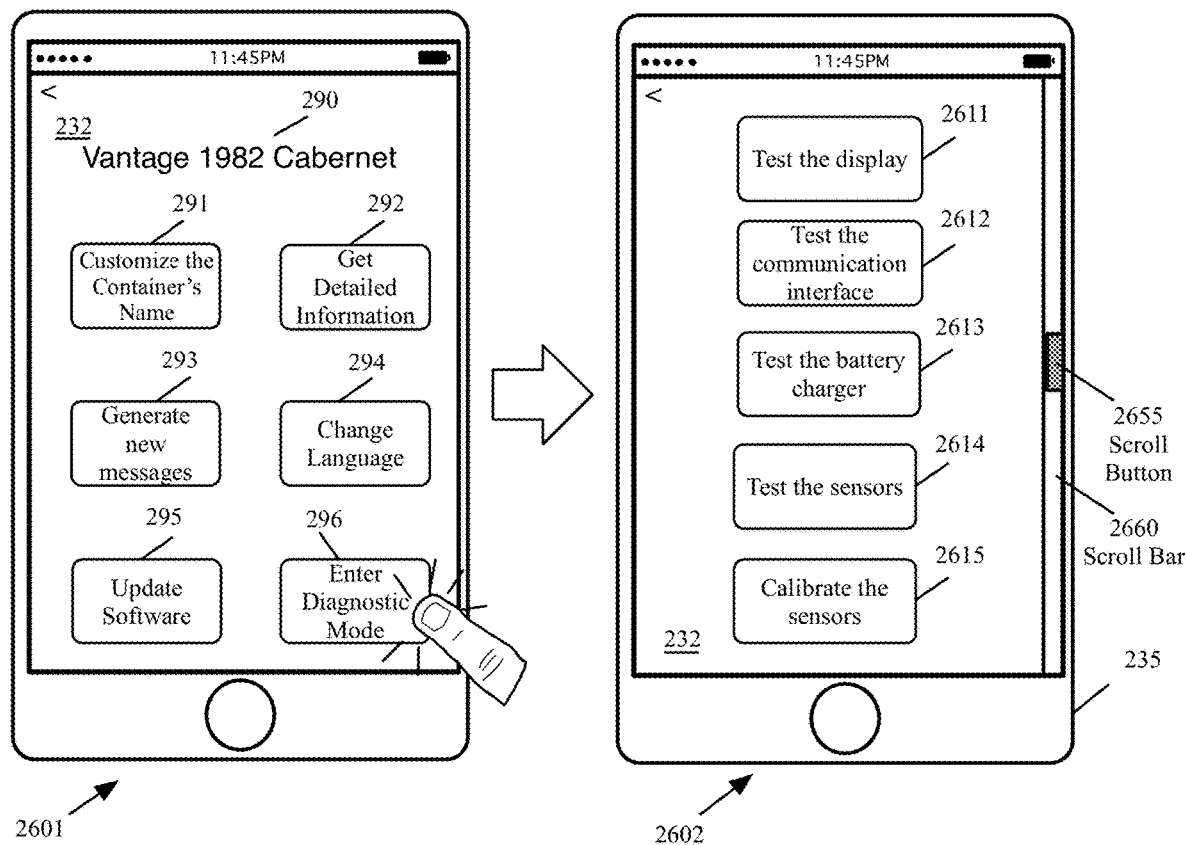
FIG. 26 illustrates a schematic front view of an electronic device that may include an application program for entering a beverage container in the diagnostic mode, according to various aspects of the present disclosure.

Some embodiments may provide a diagnostic mode in order to troubleshoot a beverage can. FIG. 26 illustrates a schematic front view of an electronic device that may include an application program for entering a beverage container in the diagnostic mode, according to various aspects of the present disclosure. The electronic device 235 of FIG. 26 may be communicatively coupled with any of the beverage containers 101-103 through a wired connection (e.g., through the USB port 1110 and cable 1130 of FIGS. 11A-11B) or a wireless connection (e.g., through the e.g., through the Bluetooth transceiver, the Wi-Fi transceiver, the IR transceiver, and/or the NFC chip described above).

The figure, as shown, includes two stages 2601 and 2602. Stage 2601 may display similar options 291-296 as stage 204 of FIG. 2. As shown in stage 2601, the option to enter diagnostic mode 296 may be selected. In response, several option 2611-2615 may be displayed on the UI 1132. In the example of FIG. 26, the displayed options for diagnostics tests include test the display 2611, test the communication interface 2612, test the battery charger 2613, test the sensors 2614, and calibrate the sensors 2615. Additional diagnostic tests may be displayed by scrolling the scroll button 2655 on the scroll bar 2660. The options may include an option (not shown) to reset the processor and other electronic components of the beverage container to a known state.

With further reference to FIG. 26, test the display option 2611 may cause one or more test patterns to be displayed by the processor 121 (FIGS. 1A-1C) of the beverage container on the display 115 of the beverage container 101-103. The patterns may be stored on the memory 122 of the beverage container 101-103 and/or may be sent from the electronic device 235 to the beverage container's processor 121.

The processor 121 may also play one or more animations on the display 115. The animations may be stored on the memory 122 of the beverage container 101-103 and/or may be sent from the electronic device 235 to the beverage container's processor 121. The processor 121 may also play one or more sounds or melodies on the speakers (e.g., the speaker 840-850 of FIG. 8). The sounds or melodies may be stored on the memory 122 of the beverage container 101-103 and/or may be sent from the electronic device 235 to the beverage container's processor 121. The results of the display and speakers tests may be automatically tested and/or the results of tests may be confirmed based on receiving user feedbacks from the beverage container 101-103 and/or from the electronic device 235.

With continued reference to FIG. 26, test the communication interface option 2612 may be performed by sending one or more predetermined signals from the electronic device 235 to the processor 121 of the beverage container and determine whether a predetermined response is received at the electronic device 2612 from the beverage container. Testing the communication interface may include testing the wireless transceiver(s) 124 and/or the NFC 125.

Test the battery charger option 2613 may include instructing the user of the electronic device to bring the electronic device 235, or another electronic device with a wireless power source, to the proximity of the beverage container and determine whether the charge level of the battery 123 of the beverage container increases. Test the sensors option 2614 may test different sensors such as the GPS 126, the temperature sensor 127, the IMU, the quality sensor(s) 129, the light source (FIG. 12B), the light sensor 1220 (FIG. 12B), the distance sensor 1810 (FIG. 18), and/or the pressure sensor 1820 (FIG. 18) as may be applicable to the particular beverage container being tested. The diagnostic test may also include inquiring the sensors and/or the processor to provide the results of their self-test (if any).

Calibrate the sensors option 2615 may be used to calibrate one or more sensors to a predetermined state as may be applicable to a particular sensor. Other tests performed during diagnostics testing may include writing known patterns to the memory and reading the values back. Some of the tests may test a combination of several components of the beverage container. For example, the beverage container may be tilted to determine whether the IMU 128 correctly senses that the beverage container is tilted, and the display may be tested whether the processor has correctly adjusted the display to compensate for the tilt.

In a first aspect, a wine bottle, comprises: a quality sensor configured to measure a set of one or more quality parameters comprising at least one of an acidity of wine and an oxidation level of wine; a processor communicatively coupled to the quality sensor; a first compartment configured to hold a first quantity of wine; a second compartment configured to: hold a second quantity of wine; encompass at least a portion of the quality sensor to bring the quality sensor in contact with the wine in the second compartment; wherein the second compartment comprises an opening to the inside of the wine bottle, and wherein the opening of the second compartment is sealed after the second quantity of the wine and said at least a portion of the quality sensor are placed in the second compartment; a third compartment configured to encompass the processor; a flexible display attached to an outside of the bottle and communicatively coupled to the processor; wherein the processor is configured to: receive the set of quality parameters from the quality sensor; and display the set of quality parameters and a set of one or more messages on the display.

An embodiment of the first aspect, where the set of messages is in a first language, further comprises: a global positioning system (GPS) receiver configured to receive a location of the wine bottle; wherein the processor is further configured to: receive the location of the wine bottle from the GPS receiver; select a second language based on the location of the wine bottle, the second language different than the first language; and replace the set of messages in the first language with the set of messages in the second language on the display.

Another embodiment of the first aspect, where the set of messages is in a first language, further comprises: a communication transceiver; wherein the processor is further configured to: receive, through the communication transceiver, a location of the wine bottle from an electronic device external to the wine bottle; select a second language based on the location of the wine bottle, the second language different than the first language; and replace the set of messages in the first language with the set of messages in the second language on the display.

Another embodiment of the first aspect further comprises: a temperature sensor communicatively coupled to the processor; wherein the processor is configured to: receive temperature measurements from the temperature sensor; and display the temperature measurements on the display.

In an embodiment of the first aspect, the temperature sensor is one of a thermistor and a thermocouple.

Another embodiment of the first aspect further comprises: a battery configured to provide power to the processor; a display port communicatively coupled to the processor, wherein the display port is connected to the display by a set of one or more wires, wherein the display port is configured to: provide power from the battery to the display; receive the set of quality parameters and the set of messages from the processor; and send the set of quality parameters and the set of messages to the display.

In another embodiment of the first aspect, the display is a touch sensitive display, and the display is configured to turn on and off in response to receiving a touch on the screen.

Another embodiment of the first aspect further comprises: a space between an interior wall of the wine bottle and the first, second, and third compartments; wherein the set of wires connecting the display port and the display passes through said space and connects to the display through a hole in a wall of the wine bottle, where the hole is air tightly sealed around the wire.

Another embodiment of the first aspect, where the set of messages is a first set of messages, further comprises a communication transceiver; wherein the processor is configured to: establish a communication channel with a set of one or more electronic devices external to the wine bottle; receive, through the communication transceiver, a second set of one or more messages from an external electronic device in the set of external electronic devices; and display the second set of one or more messages on the display.

In an embodiment of the first aspect, the communication transceiver comprises one of a near field communication (NFC) chip, a Bluetooth transceiver, and a Wi-Fi transceiver.

Another embodiment of the first aspect further comprises a communication transceiver; wherein the processor is configured to: establish a communication channel with a set of one or more electronic devices external to the wine bottle; and send, through the communication transceiver, the set of quality parameters and the set of messages to the set of external electronic devices.

Another embodiment of the first aspect further comprises a cork that caps an opening in the first compartment; an empty space between an interior of the wine bottle and at least a portion of the first compartment; a wire going through the cork and making a closed loop with the processor, wherein the wire is configured to break when the cork is removed from the opening of the first compartment; and wherein the processor is configured to: detect that the wire is broken; and in response to detecting that the wire is broken, display a message on the display indicating that the cork has been removed from the first compartment.

Another embodiment of the first aspect further comprises a cork that caps an opening in the first compartment; and a light emitter and a light sensor positioned on opposite sides of the cork; wherein the light sensor is configured to: receive light from the light emitter when the cork is removed; and in response to receiving the light from the light emitter, send a signal to the processor; wherein the processor is configured to: receive the signal from the light sensor; and in response to receiving the signal from the light sensor, display a message on the display indicating that the cork has been removed from the first compartment.

Another embodiment of the first aspect further comprises a rechargeable battery configured to provide power to the processor; a near field communication (NFC) chip configured to: communicatively couple the processor to a set of one or more electronic devices external to the wine bottle; and charge the battery through a wireless link with an external device.

Another embodiment of the first aspect further comprises a bottom side opposite to an opening of the first compartment, wherein the wine bottle comprises an empty space between the first compartment and the bottom side of the wine bottle; a removable cap configured to position in at least two states; wherein in a first state, the cap is removed from the bottom side of the wine bottle to provide access to the second and third compartments; and wherein in a second state, the cap seals the bottom side of the wine bottle.

In another embodiment of the first aspect, the second compartment is filled with wine when the removable cap is removed from the bottom side of the wine bottle.

In another embodiment of the first aspect, the opening of the second compartment is sealed with an expendable substance comprising one of rubber and silicone.

In a second aspect, a beverage can comprises: an accelerometer; a processor communicatively coupled to the accelerometer; a first compartment configured to hold a quantity of carbonated beverage, the first compartment comprising a breakable tab to seal the first compartment after receiving the beverage; a second compartment separated from the first compartment by a space, the second compartment configured to: encompass the processor and the accelerometer; a flexible display attached to an outside of the beverage can and communicatively coupled to the processor; wherein the processor is configured to: receive the set of parameters measuring a shaking of the beverage can from the accelerometer; based on the parameters received from the accelerometer, determine whether the shaking of the beverage has exceeded a threshold; when the shaking of the beverage can exceeds the threshold: start a timeout period; prior to expiration of the timeout period, display one or more messages on the display to indicate the tab may not be broken; after an expiration of the timeout period, send one or more messages to the display to indicate the tab may be broken.

An aspect of the second embodiment further comprises: a temperature sensor communicatively coupled to the processor; wherein the processor is configured to: receive temperature measurements from the temperature sensor; and display the temperature measurements on the display.

In an aspect of the second embodiment, the temperature sensor is one of a thermistor and a thermocouple.

Another aspect of the second embodiment further comprises: a rechargeable battery configured to provide power to the processor; a near field communication (NFC) chip configured to: communicatively couple the processor to a set of one or more electronic devices external to the beverage can; and charge the battery through a wireless link with an external device.

Another aspect of the second embodiment, where the set of messages is a first set of messages, further comprises: a communication transceiver; wherein the processor is configured to: establish a communication channel with a set of one or more electronic devices external to the beverage can; receive, through the communication transceiver, a second set of one or more messages from an external device in the set of external devices; and display the second set of one or more messages on the display.

In another aspect of the second embodiment, the communication transceiver comprises one of a near field communication (NFC) chip, a Bluetooth transceiver, and a Wi-Fi transceiver.

Another aspect of the second embodiment further comprises: a communication transceiver; wherein the processor is configured to: establish a communication channel with a set of one or more electronic devices external to the beverage can; and send, through the communication transceiver, the set of quality parameters and the set of messages to the set of external electronic devices.

Another aspect of the second embodiment further comprises: a battery configured to provide power to the processor; a display port communicatively coupled to the processor, wherein the display port is connected to the display by a set of one or more wires, wherein the display port is configured to: provide power from the battery to the display; receive the set of quality parameters and the set of messages from the processor; and send the set of quality parameters and the set of messages to the display.

In another aspect of the second embodiment, the display is a touch sensitive display, and the display is configured to turn on and off in response to receiving a touch on the screen.

In another aspect of the second embodiment, the set of wires connecting the display port and the display passes through the space between the first and second compartments and connects to the display through a hole in a wall of the beverage, and wherein the hole is air tightly sealed around the wire.

In a third aspect, a beverage can comprises: a processor; a first compartment configured to hold a quantity of carbonated beverage, the first compartment comprising a breakable tab to seal the first compartment after receiving the beverage; a second compartment separated from the first compartment by a space, the second compartment configured to encompass the processor; a force sensing resistor communicatively coupled to the processor; an elastic pad, wherein the force sensing resistor and the elastic pad are snuggly fitted in the space between the first and second compartments such that a surface of the force sensing resistor is in contact with second compartment and the elastic pad is between the force sensing resistor and an interior of the first compartment; a flexible display attached to an outside of the beverage can and communicatively coupled to the processor; wherein the processor is configured to: receive, from the force sensing resistor, a set of parameters measuring a force applied by the second compartment to the surface of the force sensing resistor; based on the set of parameters received from the force sensing resistor, determine whether the carbonated beverage in the first compartment may spill if the tab is broken; and display one or more messages on the display of the beverage can indicating that the carbonated beverage may spill out of the tab is broken.

IX. Electronic System

The electronic devices such as the beverage containers, computers (e.g., desktop computers, laptop computers, personal computers, tablet computers, server computers, mainframes, blade computers etc.), phones (e.g., smartphones), personal digital assistant (PDA), or any other sort of electronic devices may include memory. The memory in the above examples may be one or more units of similar or different memories. For example, the electronic devices' memory may include, without any limitations, random access memory (RAM), read-only-memory (ROM), read-only compact discs (CD-ROM), erasable programmable read-only memories (EPROMs), electrically erasable programmable read-only memories (EEPROMs), flash memory (e.g., secured digital (SD) cards, mini-SD cards, micro-SD cards, etc.), magnetic and/or solid state hard drives, ultra-density optical discs, any other optical or magnetic media, and floppy disks.

Electronic devices described above may include one or more processing units (or processors). The processing unit in above examples may be a single processor or a multi-core processor in different embodiments. The electronic devices in some of the present embodiments may store computer program instructions in the memory, which may be a machine-readable or computer-readable medium (alternatively referred to as computer-readable storage medium, machine-readable medium, or machine-readable storage medium). The computer-readable medium may store a program that is executable by at least one processing unit and includes sets of instructions for performing various operations. Examples of programs or computer code include machine code, such as is produced by a compiler, and files including higher-level code that are executed by a computer, an electronic component, or a microprocessor using an interpreter. From these various memory units, the processing unit may retrieve instructions to execute and data to process in order to execute the processes of the present embodiments. The electronic devices may include one or more buses that may include system, peripheral, and/or chipset buses that communicatively connect the numerous internal devices of an electronic device.

As used in this disclosure and any claims of this disclosure, the terms such as "processing unit," "processor," "controller," "microcontroller," "server", and "memory" all refer to electronic or other technological devices. These terms exclude people or groups of people. For the purposes of this disclosure, the terms display or displaying means displaying on an electronic device. As used in this disclosure and any claims of this disclosure, the terms "computer readable medium," "computer readable media," and "machine readable medium" are entirely restricted to tangible, physical objects that store information in a form that is readable by a processing unit. These terms exclude any wireless signals, wired download signals, and any other ephemeral or transitory signals.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented, and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A beverage can, comprising:
   an accelerometer;
   a processor communicatively coupled to the accelerometer;
   a first compartment configured to hold a quantity of carbonated beverage, the first compartment comprising a breakable tab to seal the first compartment after receiving the beverage;
   a second compartment separated from the first compartment by a space, the second compartment configured to:
   encompass the processor and the accelerometer;
   a flexible display attached to an outside of the beverage can and communicatively coupled to the processor;
   wherein the processor is configured to:
   receive a set of parameters measuring a shaking of the beverage can from the accelerometer;
   based on the parameters received from the accelerometer, determine whether the shaking of the beverage has exceeded a threshold;

when the shaking of the beverage can exceeds the threshold:
start a timeout period;
prior to expiration of the timeout period, display one or more messages on the display to indicate the tab may not be broken;
after an expiration of the timeout period, send one or more messages to the display to indicate the tab may be broken.

2. The beverage can of claim 1, further comprising:
a temperature sensor communicatively coupled to the processor;
wherein the processor is configured to:
receive temperature measurements from the temperature sensor; and
display the temperature measurements on the display.

3. The beverage can of claim 1 further comprising:
a rechargeable battery configured to provide power to the processor;
a near field communication (NFC) chip configured to:
communicatively couple the processor to a set of one or more electronic devices external to the beverage can; and
charge the battery through a wireless link with an external device.

4. The beverage can of claim 1, wherein the one or more messages is a first set of messages, the beverage can further comprising:
a communication transceiver;
wherein the processor is configured to:
establish a communication channel with a set of one or more electronic devices external to the beverage can;
receive, through the communication transceiver, a second set of one or more messages from an external device in the set of external devices; and
display the second set of one or more messages on the display.

5. The beverage can of claim 4, wherein the communication transceiver comprises one of a near field communication (NFC) chip, a Bluetooth transceiver, and a Wi-Fi transceiver.

6. The beverage can of claim 1, further comprising:
a communication transceiver;
wherein the processor is configured to:
establish a communication channel with a set of one or more electronic devices external to the beverage can; and
send, through the communication transceiver, a set of quality parameters and the one or more messages to the set of external electronic devices.

7. The beverage can of claim 1, further comprising:
a battery configured to provide power to the processor;
a display port communicatively coupled to the processor, wherein the display port is connected to the display by a set of one or more wires, wherein the display port is configured to:
provide power from the battery to the display; and
receive the set of quality parameters and the set of messages from the processor; and
send the set of quality parameters and the set of messages to the display.

8. The beverage can of claim 7, wherein the display is a touch sensitive display, and wherein the display is configured to turn on and off in response to receiving a touch on the screen.

9. The beverage can of claim 7, wherein the set of wires connecting the display port and the display passes through the space between the first and second compartments and connects to the display through a hole in a wall of the beverage can, and wherein the hole is air tightly sealed around the wire.

\* \* \* \* \*